United States Patent [19]

Queener et al.

[11] Patent Number: 5,543,497
[45] Date of Patent: Aug. 6, 1996

[54] GENES ENCODING AND METHOD OF EXPRESSING A NOVEL ENZYME: PHTHALYL AMIDASE

[75] Inventors: Stephen W. Queener, Indianapolis; Joseph M. Zock, Greenwood, both of Ind.

[73] Assignee: Eli Lilly and Company, Indianapolis, Ind.

[21] Appl. No.: 446,382

[22] Filed: May 22, 1995

Related U.S. Application Data

[62] Division of Ser. No. 275,490, Jul. 15, 1994, Pat. No. 5,451,522.
[51] Int. Cl.$^6$ .............................. C12N 9/80; C12N 15/74
[52] U.S. Cl. .................... 530/324; 930/300; 536/24.1; 935/6; 435/228
[58] Field of Search .................... 930/300; 530/324; 536/24.1; 935/6; 435/228

[56] References Cited

U.S. PATENT DOCUMENTS 4,977,089  12/1990  Kovacevic et al. ................. 435/252.3
5,032,510  7/1991  Kovacevic et al. .................... 435/69.1

OTHER PUBLICATIONS

Smith, Gale E., et al., *Molecular and Cellular Biology*, vol. 3, No. 12, pp. 2156–2165, Dec. 1983.

Yang et al., *Journal of Biological Chemistry*, vol. 268, No. 15, pp. 10870–10875, 1993.

*Primary Examiner*—Robert A. Wax
*Assistant Examiner*—Keith D. Hendricks
*Attorney, Agent, or Firm*—Donna K. Blalock; Paul R. Cantrell; David E. Boone

[57] ABSTRACT

Phthalyl amidase is an enzyme previously unknown in the art that catalyzes removal of the phthalyl moiety from phthalyl-containing amides. The current invention provides DNA compounds encoding the phthalyl amidase enzyme and methods for expressing such compounds. The present invention also provides recombinant DNA vectors encoding phthalyl amidase and host cells transformed with these DNA vectors.

4 Claims, 2 Drawing Sheets

Function and restriction map of plasmid vector pZPA600.
Abbreviations:
PAorf = phthalyl amidase open reading frame.
tsr = gene enabling resistance to thiostrepton.

Function and restriction map of plasmid
vector pZPA400.
Abbreviations:
PA-orf = phthalyl amidase open reading frame.
pL97-pro = modified promoter from phage lamda.
tet = gene enabling resistance to thiostrepton.
cI857 = gene encoding temperature sensitive lamda
repressor.

GENES ENCODING AND METHOD OF EXPRESSING A NOVEL ENZYME: PHTHALYL AMIDASE

This application is a division of application Ser. No. 08/275,490, filed Jul. 15, 1994, now U.S. Pat. No. 5,451,522.

BACKGROUND OF THE INVENTION

The present invention relates to the discovery of a specific enzyme that has not been previously described, a phthalyl amidase which readily removes the phthalyl moiety from phthalyl-containing amides. The present invention also relates to an organism isolated from natural sources that produces the enzyme, DNA compounds that encode the enzyme, and methods for producing and using the enzyme.

The phthalimido functional group is an important tool in organic synthesis because of the protection it provides against unwanted reactions. However, dephthalylation reactions generally require harsh conditions and often have low yields thereby limiting the situations in which phthalimido protection can be employed.

Removal of a phthalyl protecting group from a phthalyl amide can be accomplished chemically, Kukolja et al., Croatica Chemica Acta 49:779, 1977, but yields are variable especially with substrates that are unstable to harsh reaction conditions.

Certain enzymes have previously been found that could be used to remove benzoyl groups from benzoylated amino acids. Toyoura et al., Chem. Pharm. Bull. 7:789, 1959. These enzymes were specific for benzoyl groups and for the amino acid to which they were attached. Others have also reported enzymes that will hydrolyze phthalate esters. Kurane et al., Agric. Biol. Chem. 44:529, 1980. However, none of these enzymes have been shown to operate on phthalyl amides.

In contrast, the phthalyl amidase enzyme of this invention catalyzes removal of the phthalyl group from a wide variety of phthalyl-containing compounds with improved yields over processes known in the art, exhibits stereochemical selectivity, and eliminates the need for harsh conditions to remove the protecting group.

SUMMARY OF THE INVENTION

The present invention provides a recombinant phthalyl amidase enzyme, which catalyzes the following type of reaction:

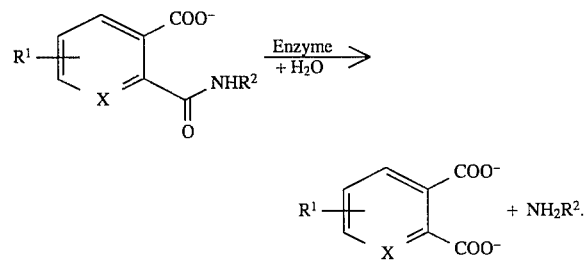

The present invention also provides DNA compounds that comprise isolated nucleotide sequences encoding the phthalyl amidase enzyme and methods for expressing such compounds. The present invention also provides recombinant DNA vectors encoding phthalyl amidase and host cells transformed with these DNA vectors. Preferred DNA compounds comprise and isolated nucleotide sequence encoding SEQ ID NO:2, especially SWQ ID NO:1 isolated from *Xanthobacter agilis*. Other preferred compounds of the present invention include DNA compounds that comprise isolated DNA sequences encoding the proenzyme form of phthalyl amidase enzyme (SEQ ID NO:4), including SEQ ID NO:3, SEQ ID NO:5, and the phthalyl amidase gene of *Xanthobacter agilis* (SEQ ID NO:6). DNA compounds of the current invention include recombinant DNA vectors, including expression vectors, which may be used to transform host cells.

The present invention also provides for DNA sequences of the naturally-occurring phthalyl amidase gene that control transcription, translation, and extra-cellular secretion of proteins. Thus, the present invention includes SEQ ID NO:7, SEQ ID NO:8, and SEQ ID NO:10.

Definitions

Coding sequence—the sequence of DNA in the open reading frame of a gene that encodes the amino acid residue sequence of the protein expressed from the gene.

Gene—a segment of DNA that comprises a promoter, translational activating sequence, coding sequence, and 3' regulatory sequences, positioned to drive expression of the gene product.

Promoter—a DNA sequence that directs or initiates the transcription of DNA.

Recombinant DNA vector—any autonomously replicating or integrating DNA agent, including but not limited to plasmids, comprising a promoter and other regulatory sequences positioned to drive expression of a DNA sequence that encodes a polypeptide or RNA.

Recombinant DNA sequence—any DNA sequence, excluding the host chromosome from which the DNA is derived, which comprises a DNA sequence that has been isolated, synthesized, or partially synthesized.

Restriction fragment—any linear DNA molecule generated by the action of one or more restriction enzymes.

Translation activating sequence—a regulatory DNA sequence that, when transcribed into mRNA, promotes translation of mRNA into protein.

All nucleotide and amino acid abbreviations used in this disclosure are those accepted by the United States Patent and Trademark Office as set forth in 37 C.F.R. §1.822(b) (1993).

BRIEF DESCRIPTION OF THE FIGURES

The restriction enzyme and function maps presented in the drawings are approximate representations of the recombinant DNA vectors discussed herein. The restriction site information is not exhaustive. There may be more restriction enzymes sites of a given type than are actually shown on the map.

DETAILED DESCRIPTION OF THE INVENTION

Figure 1:
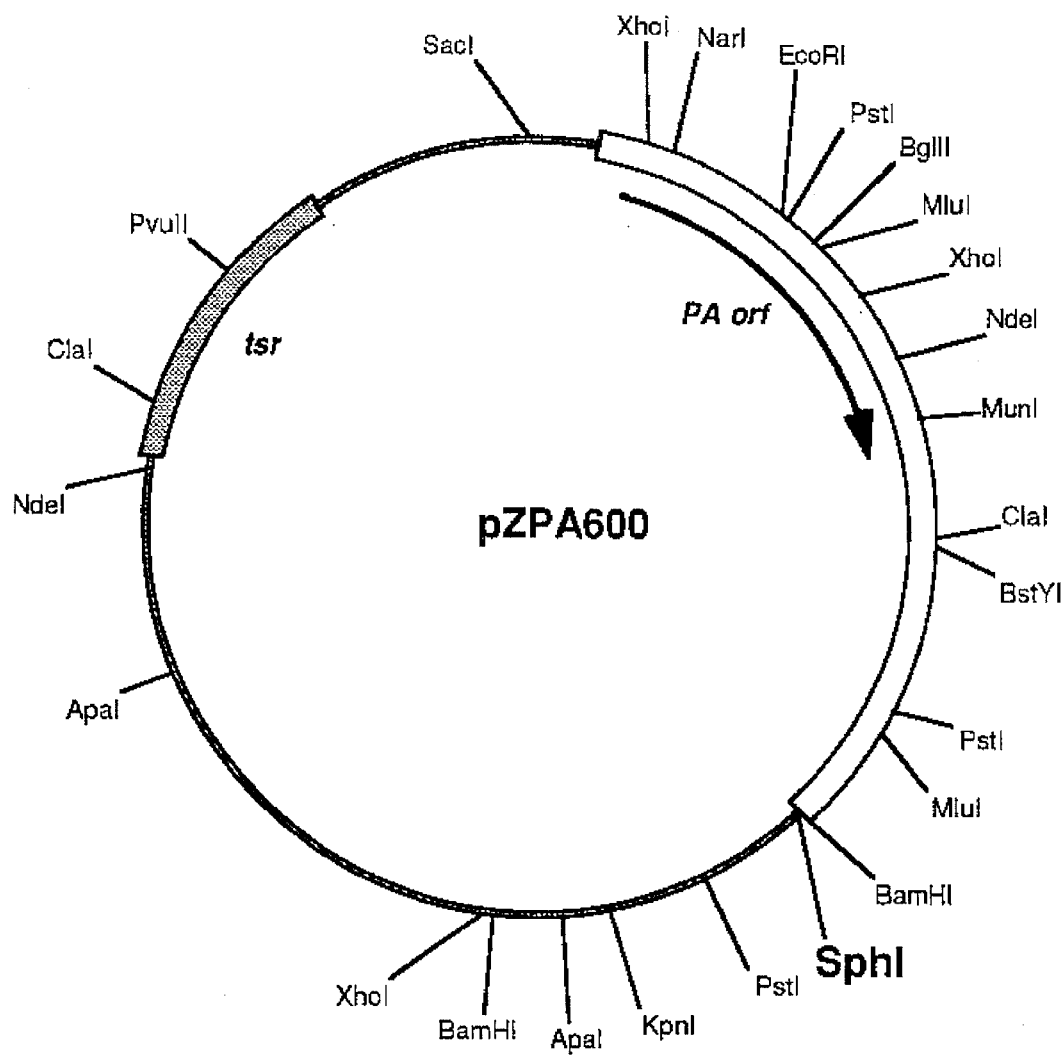
FIG. 1 is a restriction enzyme site and function map of plasmid pZPA600.

During the course of developing a chiral, shorter, and more efficient synthetic route to loracarbef ([6R-(6A, 7B(R))]-7-[(aminophenylacetyl)amino]-3-chloro-8-oxo-azabicyclo[4,2,0]oct-2-ene-2-ene-2-carboxylic acid), the Mitsunobu reaction (see e.g. Hughes, D. L. Organic reactions 42:336, 1992; Bose, A. K. et al., Can. J. Chem. 62:2498, 1984) was selected for forming the beta-lactam ring from a chiral linear amino acid ester intermediate. Several reactants with one N-valence protected and a few reactants with both N-valences protected were examined in Mitsunobu reactions. They were either not cyclized or were cyclized in poor yield.

It was discovered that problems in forming the beta-lactam ring via Mitsunobu reactions could be overcome if both valences of the α-nitrogen of the chiral linear amino acid ester intermediate were protected with a phthalimido group. However, no known chemical reaction was available to remove the phthalimido moiety and regenerate free amine in high yield.

Thus, soil samples were examined for microorganisms that could catalyze removal of the phthalamido group from a test substrate (II) that was formed by base cleavage of the phthalimido ring of a bivalently N-protected compound. A culture was identified that demonstrated phthalyl amidase activity that liberated the free amine derivative of the test substrate. Native enzyme was purified and shown to catalyze the following desired reaction:

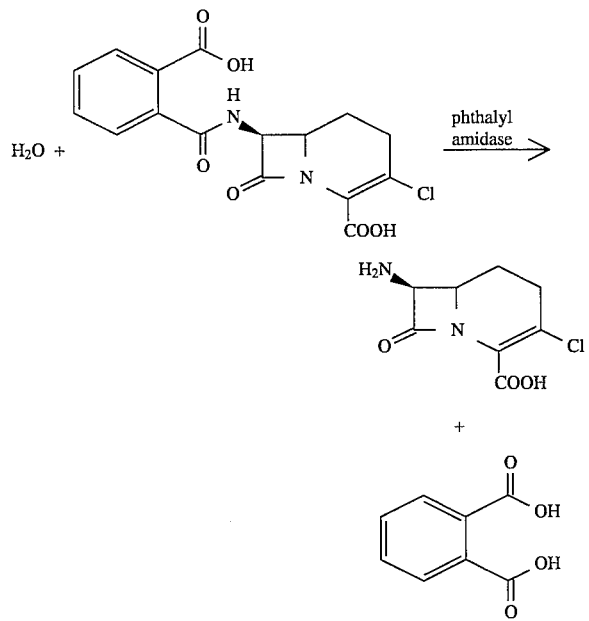

Phthalyl amidase also has significant value in peptide synthesis applications. Phthalimido amino acid derivatives are very effective reactants for enzymatic coupling of amino acids to form peptides. However, heretofore, methods for removing the phthalimido blocking group from the protected peptide were lacking. The phthalyl amidase of the current invention displays reactivity toward a wide range of substrates and can be used for deblocking phthalimido-protected peptide intermediates.

The isolated phthalyl amidase of this invention demonstrates high specific activity toward phthalylated amides or esters (i.e., having a 1,2 dicarboxylate configuration). Such compounds may have other functional groups on the phthalyl aromatic ring and still serve as substrates for the enzyme. For example, acceptable functional groups include 6-F, 6-$NH_2$, and 3-OH. Moreover, substrates may include a nitrogen in the aromatic ring ortho to the carboxyl group attached to the amine. Compounds lacking a 2-carboxylate, such as benzoyl, phenylacetate, phenoxyacetate, or their derivatives, are not suitable substrates for this enzyme.

The enzyme also exhibits a broad substrate specificity in regard to the amine group attached to the phthalate side chain. For example, phthalylated amino acids and peptides, mono- and bicyclic beta-lactams, aromatic and non-aromatic amines, as well as phthalylated amines attached to heterocycles, are dephthalylated by this enzyme at acceptable catalytic rates. The enzyme also removes the methyl group from mono-methyl phthalate.

The enzyme is stable in the broad range of pH from 6–9, having an optimum stability pH of 8.0±0.4. The enzyme also demonstrates a marked stability dependence on ionic strength. Ionic strength above 20 mM enhances pH and temperature stability of the enzyme. Optimum ionic strength occurs at 200 mM and above.

The enzyme retains good activity in low salt (50 mM) up to 30° C. and in high salt (200 mM) up to 40° C. In 200 mM salt, at least 80% of the enzyme activity is retained in temperatures up to 35° C. for 48 hours.

Iodoacetic acid (10 mM), p-HMB (1 mM), and $Cu^{++}$ (1 mM) significantly inhibited the enzyme. No organic co-factors, such as ATP, NADPH, or others, stimulated enzyme activity. EDTA, phenanthroline, and metal ions besides $Cu^{++}$ had little or no effect on enzyme activity.

The molecular weight of the enzyme is approximately 49,900, as determined by electrospray mass spectrometry, and the molecule consists of one subunit.

The $K_m$, with phthalamido carbacephem (7-phthalamido-3-chloro-4-carboxy-1-carba-dethioceph-3-em) (III) as substrate, is 0.9 mM in 50 mM potassium phosphate buffer, pH 8.0, and 30° C. The $V_{max}$ for this substrate and under these conditions is 7.6 μmol/min/mg.

Phthalyl amidase activity was recovered from a microorganism isolated from soil samples. The organism was characterized by comparison of its fatty acid methyl ester profile with that of known standards, and has been identified as a strain of *Xanthobacter agilis*.

The organism can be preserved as lyophilized culture and has been deposited with the National Center for Agricultural Utilization Research, 1815 North University St., Peoria, Ill. 61604-39999, under accession number NRRL B-21115 (date of deposit: Jun. 28, 1993). Working cultures are maintained as liquid cultures stored in liquid nitrogen or at temperatures below −78° C.

In order to recover the phthalyl amidase of this invention, *Xanthobacter agilis* can be cultivated in an aqueous nutrient medium consisting of a source of carbon and nitrogen and mineral salts at an initial pH between 6 and 8 and at 25° to 37° C. A number of agents can be included in the culture medium as inducers of enzyme production, including, for example, phthalate (PAA), phthalyl glycine (PAG), and phthalyl monocyclic beta-lactam (PMBL). The enzyme can be recovered in larger amounts by cultivating *Xanthobacter agilis* in a known manner in a bioreactor of desired size, for example, with a working volume of 100 liters. Good aerating conditions, and the presence of nutrients in complex form, and a pH between 6 and 8 are important for a successful culture. The cell mass can be separated from the medium and the enzyme purified as shown in Example 4.

It will be recognized by those skilled in the art that phthalyl amidase-producing mutants of the isolated *Xanthobacter agilis* organism can readily be made by methods known in the art. These mutants are considered within the scope of this invention.

As described, phthalyl amidase, catalyzes the removal of the phthalyl moiety from a wide range of phthalimido-containing compounds. The enzyme actually cleaves the amide bond of phthalamido substrate, which is formed by the action of mild base on the corresponding phthalimido compound. This conversion proceeds readily under conditions that are suitable for enzyme activity. Thus, the phthalimido-containing compound and the enzyme being concurrently present under conditions that promote enzyme activity result in in situ removal of the phthalyl group.

In some chemical reactions involving an amine reactant, the corresponding phthalimido compound is particularly suited to high reaction yields whereas the conversion proceeds poorly with the unprotected amine or with a monovalently protected amine or even when the amine is bivalently protected by an alternative means. Thus, the current invention, which provides an economic source of phthalyl amidase, allows practical synthesis of a variety of amine products via phthalimido-protected amine intermediates.

It will be recognized that the enzyme can also be used in immobilized form to catalyze desired reactions according to procedures known in the art.

A specific application of the current invention occurs in a new chiral synthesis of the antibiotic loracarbef. The phthalyl amidase-catalyzed reaction shown above is one step of that synthesis.

Another application occurs in the synthesis of aspartame (N-L-α-aspartyl-L-phenylalanine, 1-methyl ester) as described in Example 16 below.

In below cases phthalic anhydride (or other suitable activated forms of phthalic acid) is used to react with an intermediate containing a key amino group so that a phthalimido moiety is formed for bivalent protection of the amino group. The bivalently protected amine can then be converted efficiently to a desired intermediate. For example, cyclization of a α-phthalimido-β-hydroxy-acid to a beta-lactam, or for example, condensation of an α-phthalimido carboxy-activated amino acid with a carboxy-protected amino acid to form a dipeptide. The phthalimido moiety is hydrolyzed with mild base and the resulting phthalamido moiety is then exposed to phthalyl amidase to catalyze the removal of the phthalyl moiety and release free amine plus phthalic acid.

In addition to identification and isolation of a naturally-occurring phthalyl amidase, the current invention provides DNA compounds that comprise an isolated nucleotide sequence encoding phthalyl amidase, recombinant DNA vectors encoding phthalyl amidase, host cells transformed with these DNA vectors, and a method for producing recombinant phthalyl amidase. These elements of the current invention provide the opportunity to use phthalyl amidase as a biocatalyst in industrial scale chemical processes.

Phthalyl amidase may be produced by cloning DNA encoding phthalyl amidase into a variety of vectors by means that are well known in the art. A number of suitable vectors may be used, including cosmids, plasmids, bacteriophage, and viruses. One of the principle requirements for such a vector is that it be capable of reproducing itself and transforming a host cell.

Preferably, the vector will be a recombinant DNA vector that is capable of driving expression of phthalyl amidase encoded by the DNA compounds of this invention. Typical expression vectors comprise a promoter region, a 5'-untranslated region, a coding sequence, a 3'-untranslated region, an origin of replication, a selective marker, and a transcription termination site.

After the DNA compound encoding phthalyl amidase has been inserted into the vector, the vector may be used to transform a host cell. In general, the host cell may comprise any cellular organism, including a prokaryotic cell or eukaryotic cell, that is capable of being transformed with a vector comprising the DNA of this invention. The techniques of transforming and transfecting cells are well known in the art and may be found in such general references as Maniatis, et al. (1989) of Current Protocols in Molecular Biology (1989).

A particularly preferred method of the current invention generates soluble, extra-cellular enzyme. The method makes use of a DNA compound that comprises SEQ ID NO:6, which enables, when transformed into Streptomyces lividans as part of a self-replicating vector, the host to produce and secrete soluble mature phthalyl amidase in an amount in excess of the amount of a cell-bound form of the enzyme produced by Xanthobacter agilis, the bacterium from which the DNA compound was cloned.

SEQ ID NO:6 comprises four functional components: SEQ ID NO:7; SEQ ID NO:8; SEQ ID NO:1; and SEQ ID NO:10. SEQ ID NO:7, which includes the promoter-bearing nucleotides 1–135 of SEQ ID NO:6, promotes transcription of the coding sequences. SEQ ID NO:8 (nucleotides 136–261 of SEQ ID NO:6) encodes the signal peptide portion of a proenzyme form of phthalyl amidase (pro-phthalyl amidase (SEQ ID NO:4)). The signal peptide (SEQ ID NO:9), which provides for transport of the proenzyme across the microbial cell wall of Streptomyces lividans, is cleaved from the proenzyme by the cell, thereby enabling extracellular production of the mature enzyme. SEQ ID NO:1 (nucleotides 262–1620 of SEQ ID NO:6) encodes mature phthalyl amidase (SEQ ID NO:2). SEQ ID NO:10 (nucleotides 1621–3029 of SEQ ID NO:6) is a 3'-untranslated region which assists proper and efficient translation termination of the mRNA that encodes pro-phthalyl amidase.

Moreover, in a more general application of the expression method of the current invention, a wide variety of soluble, extra-cellular, properly-folded, functional proteins may be produced in Streptomyces. The current method comprises propagating Streptomyces lividans that has been transformed with a DNA compound, which encodes the desired enzyme, protein, or peptide, and which includes the transcriptional and translational regulatory elements of the phthalyl amidase gene isolated from the bacterium Xanthobacter agilis. These regulatory elements enable synthesis and secretion of the soluble, properly-folded, functional enzyme, protein, or peptide.

To accomplish the general method, the DNA sequence encoding mature phthalyl amidase (SEQ ID NO:1) may be replaced in SEQ ID NO:6 by a heterologous open reading frame from a wide variety of organisms wherein the heterologous open reading frame encodes a mature protein or hormone and introns are absent from those open reading frames, either by nature or by virtue of precise removal from genomic DNA to form cDNA open reading frames. In this arrangement, the regulatory elements of the phthalyl amidase gene continue to function such that proteins and oligopeptides other than phthalyl amidase are produced and secreted from Streptomyces transformed with the modified DNA sequence. Thus, substitution of a desired protein-encoding sequence for the coding sequence of mature phthalyl amidase enables economic extra-cellular production of numerous enzymes, peptides, and peptide hormones.

Synthesis of the phthalyl amidase gene and its various elements can be accomplished by recombinant DNA technology. Synthetic genes, the in vitro or in vivo transcription and translation of which will result in the production of the phthalyl amidase enzyme, may be constructed by techniques well known in the art. Owing to the degeneracy of the genetic code, the skilled artisan will recognize that a sizable, yet definite, number of DNA sequences may be constructed, which encode the phthalyl amidase enzyme. All such sequences are provided by the present invention.

A preferred sequence encoding phthalyl amidase is the naturally-occurring phthalyl amidase gene of *Xanthobacter agilis*, which is SEQ ID NO:6. This preferred gene is available on an 3.2 kb SacI-BamHI restriction fragment of plasmid pZPA600, which can be isolated from *Streptomyces lividans* TK23/pZPA600 by techniques well known in the art. *Streptomyces lividans* TK23/pZPA600 designates *Streptomyces lividans* strain TK23 which has been transformed with vector pZPA600.

Plasmid pZPA600 was derived by ligating SEQ ID NO:6 into Streptomyces vector, pIJ702 (Hopwood, D. A., et al., *Genetic Manipulations of Streptomyces: A Laboratory Manual*. The John Innes Foundation, Norwich, England, 1985). The pIJ702 vector contains a pIJ101 Streptomyces replicon and a thiostrepton resistance gene for selection. The ligated material was transformed into *Streptomyces lividans* TK23 by a standard protoplast fusion technique. After selection on thiostrepton (45 µg/ml), the plasmid designated pZPA600, was isolated and confirmed by restriction analysis. A restriction site and function map of plasmid pZPA600 is found in FIG. 1.

*Streptomyces lividans* TK23/pZPA600 is publicly available and on deposit at the National Center for Agricultural Utilization Research, 1815 North University St., Peoria, Ill. 61604-39999, under accession number NRRL B21290 (date of deposit: Jun. 23, 1994). The *Streptomyces lividans* TK23 strain has been previously described in *Plasmid* 12:1936 (1984).

Plasmid pZPA600 allows high level expression of the pro-phthalyl amidase open reading frame and results in secretion of soluble mature phthalyl amidase, which process is especially preferred. Thus, the invention comprises a process in which *Streptomyces lividans* TK23/pZPA600 is grown and then separated from its extra-cellular broth so that high concentrations of phthalyl amidase are obtained in that cell-free broth.

Other preferred sequences include, for example, SEQ ID NO:1, which encodes mature phthalyl amidase enzyme (SEQ ID NO:2), and SEQ ID NO:3, which encodes the proenzyme form of phthalyl amidase (SEQ ID NO:4). Thus, the present invention also comprises plasmid pZPA400 as a preferred embodiment.

Figure 2:
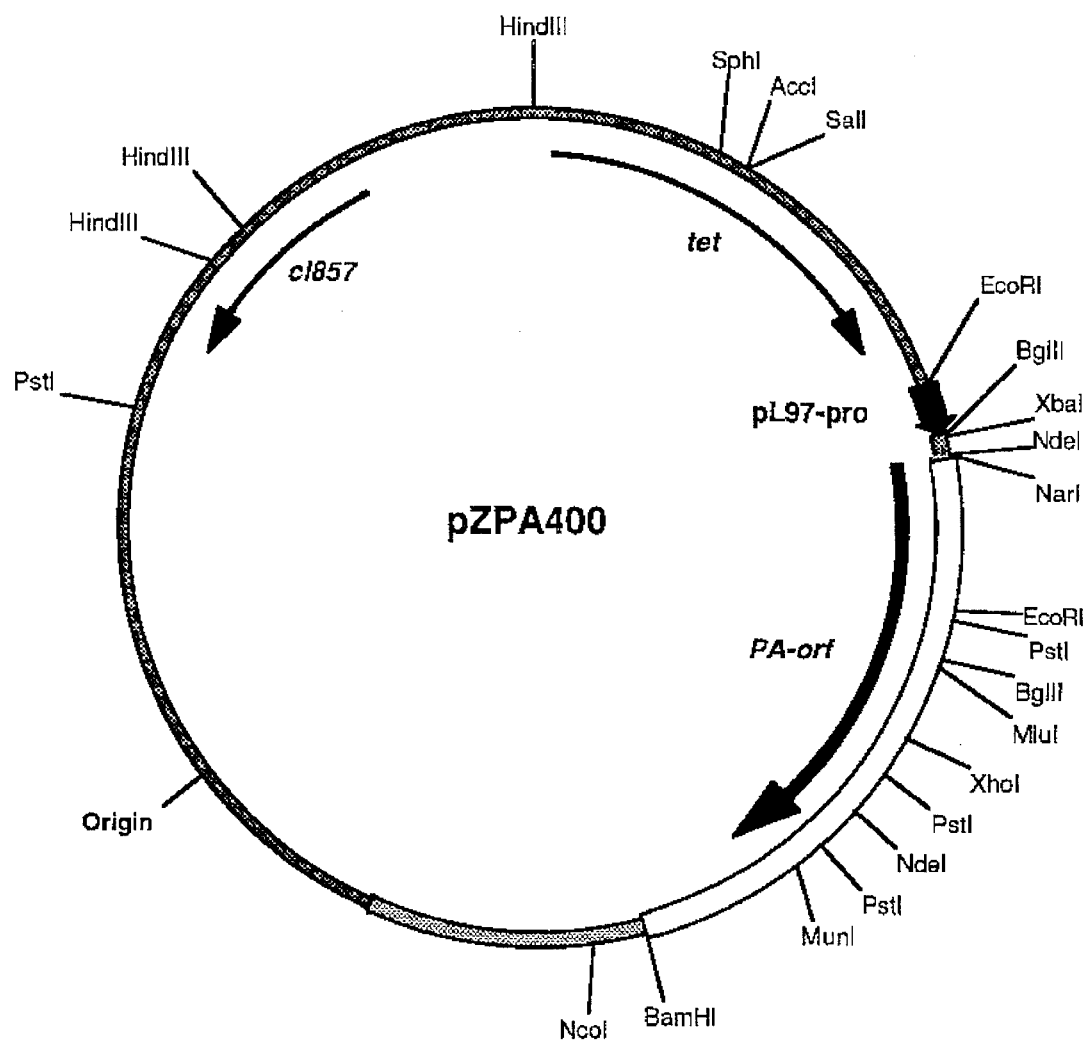
FIG. 2 is a restriction enzyme site and function map of plasmid pZPA400.

In plasmid pZPA400, the 5'-regulatory elements of the native gene were removed and an ATG codon for a methionyl residue was attached to the 5'-terminal nucleotide of the mature phthalyl amidase coding sequence to generate an open reading frame (SEQ ID NO:11) encoding met-phthalyl amidase (SEQ ID NO:12). SEQ ID NO:11 was positioned, via a two-cistron configuration, such that transcription was driven by a temperature inducible lambda pL promoter. Plasmid pZPA400 also contains the temperature sensitive cI857 repressor gene, a tetracycline resistance gene, and the pBR322-based origin of replication minus the rop region, which controls copy number (Cesareni et al., Proc. Natl. Acad. Sci. 79:6313, 1982). *E. coli* cells harboring this plasmid (*E. coli* DH5α/pZPA400) are induced to produce met-phthalyl amidase (without signal peptide) when the culture temperature is raised from 30° C. to 42° C. A restriction site and function map of plasmid pZPA400, which can be isolated from *E. coli* DH5α/pZPA400 cells by techniques well known in the art, is found in FIG. 2.

*E. coli* DH5α/pZPA400 designates the commercially available *E. coli* DH5α strain that has been transformed with plasmid pZPA400. *E. coli* DH5α/pZPA400 cells are publicly available and on deposit at the National Center for Agricultural Utilization Research, 1815 North University Street, Peoria, Ill. 61604-39999, under accession number NRRL 21289 (date of deposit Jun. 23, 1994).

The phthalyl amidase gene may also be created by synthetic methodology. Such methodology of synthetic gene construction is well known in the art. See Brown et al. (1979) *Methods in Enzymology*, Academic Press, N.Y., 68:109. The phthalyl amidase DNA sequence may be generated using a conventional DNA synthesizing apparatus, such as the Applied Biosystems Model 380A of 380B DNA synthesizers (commercially available from Applied Biosystems, Inc., 850 Lincoln Center Drive, Foster City, Calif. 94404.

Synthesis of the phthalyl amidase protein of the present invention may also proceed by solid phase synthesis. The principles of solid phase chemical synthesis of polypeptides are well known in the art and may be found in general texts, such as, Dugas, H. and Penny, C., *Bioorganic Chemistry* (1981), Springer-Verlag, New York, pp. 54–92. However, recombinant methods are preferred if a high yield is desired.

A skilled artisan will recognize that the nucleotide sequences described in the present disclosure may be altered by methods known in the art to produce additional sequences that substantially correspond to the described sequences without changing their functional aspects. These altered sequences are considered to be included in the current invention.

In order that the invention described herein may be more fully understood, the following examples are set forth. It should be understood that the examples are for illustrative purposes only and are not to be construed as limiting the scope of the invention.

EXAMPLE 1

Search for phthalyl amidase producing organisms 240 soil samples (8 to 15 mg of damp dry soil) were individually suspended in 10 ml sterile BL medium (hereinafter defined) containing 100 mg phthalyl monocyclic beta-lactam (PMBL) (I).

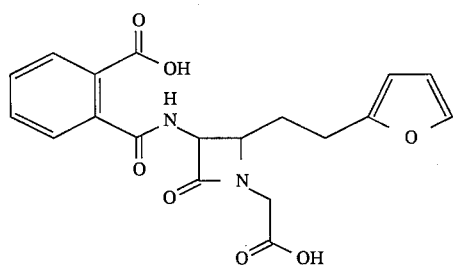

BL medium had the following composition:

| | |
|---|---|
| $Na_2HPO_4$ | 6.0 g |
| $KH_2PO_4$ | 3.0 g |
| NaCl | 0.5 g |
| $NH_4Cl$ | 2.0 g |
| $CaCl_2$ | 0.1 g |
| $MgSO_4 \cdot 7H_2O$ | 0.25 g |
| $ZnSO_4 \cdot 7H_2O$ | 70 mg |
| $FeCl_3 \cdot 5H_2O$ | 270 mg |

9
-continued

| | |
|---|---|
| MnSO$_4$ | 80 mg |
| CuCl$_2$ | 7.4 mg |
| CoSO$_4$.7H$_2$O | 28 mg |
| H$_3$BO$_3$ | 3 mg |
| Yeast Extract | 1.0 g |
| Deionized water | 1.0 L |
| pH | 7.0 |

The cultures were incubated aerobically at 30° C. in a rotary shaker at 250 rpm for as long as 2 weeks. Cultures were examined by thin layer chromatography at 7 day intervals for the disappearance of the starting substrate and appearance of the beta-lactam nucleus product.

A culture showing the desired catalytic activity was transferred at least two more times under similar conditions of medium and growth. The final culture was diluted with sterile water and plated out on agar plates containing either Trypticase Soy Broth (Difco) or Bac MI medium. Bac MI medium had the following composition:

| | |
|---|---|
| Peptone | 10.0 g |
| Beef Extract | 5.0 g |
| Yeast Extract | 2.0 g |
| NaCl | 5.0 g |
| Deionized water | 1.0 L |
| pH | 7.0 |

(Agar plates were prepared by adding 20 g agar per L of medium).

Individual colonies were picked from the agar and grown in Bac MI medium containing 10 mg/ml of PMBL for 12 days at 30° C. with aeration. Broths were examined for appearance of beta-lactam nucleus and phthalic acid using TLC.

A pure isolated organism that demonstrated rapid hydrolysis of the substrate was then grown in Bac MI medium containing 1 mg/ml phthalate for 48 hours at 30° C. with aeration. Cells were centrifuged and then suspended in 50 mM Tris-HCl buffer, pH 8.0, at a ratio of 1 g wet weight cells to 8 ml of buffer. A solution of lysozyme, 2 mg in 1.0 ml 50 mM EDTA, pH 8.2, was added at the ratio of 1 ml lysozyme solution to 8 ml cell suspension. After mixing well and holding at room temperature for 1 hour, the suspension was cooled to 4° C. and held overnight. The resultant viscous solution was sonicated only long enough to liquefy the solution. This solution was centrifuged at 10,000 rpm for 15 minutes. The pellet was discarded and the supernatant tested for phthalyl amidase activity.

The cell-free extract was chromatographed on a size exclusion column (1.5×100 cm; Sephacryl S-300; Pharmacia, Piscataway, N.J.) at 4° C. with an elution buffer consisting of 50 mM potassium phosphate and 150 mM KCl at a flow rate of 0.5 ml/min. The eluant was monitored at a wavelength of 280 nm. UV-absorbing fractions were tested for hydrolysis of PMBL by HPLC.

Reference proteins for molecular weight (daltons) determination were chymotrypsinogen (25,000), ovalbumin (43,000), albumin (67,000), aldolase (158,000), catalase (232,000), ferritin (440,000), and thyroglobulin (669,000).

Cell-free extract of the organism subsequently identified as *Xanthobacter agilis* was determined to contain an enzyme that catalyzed the hydrolysis of PMBL, and which had an approximate molecular weight of 54,000 daltons and a specific activity of 39.7 nmol/min/mg.

10
EXAMPLE 2

Production of phthalyl amidase from *Xanthobacter agilis*

Fermentation of *Xanthobacter agilis* on a 100 L scale was conducted in 100 L working volume bioreactors, with automatic control for pH (7.9–8.1), temperature (30° C.), air flow (1 scfm), agitation (300 rpm), and back pressure (5 lb). Dissolved oxygen levels (>50%) were kept constant by small increases in agitation speed. The medium consisted of 1.25% Bacto peptone, 0.3% yeast extract, 0.5% beef extract, 0.5% phthalic acid, 0.5% NaCl, and 0.05% anti-foam. After sterilization, the medium was brought to pH 8.0 with 30% sulfuric acid. The fermenter was inoculated with 1 L of pre-culture which had been incubated at 30° C. for 24 hours in the same medium with shaking at 300 rpm. After 48 hours of growth, the fermentation broth was cooled and centrifuged at 17,000 rpm with a flow rate of 1 to 2 L/min to remove the biomass. The cell paste was harvested and stored at −20° C. yielding 6.0 g wet cell weight/L.

EXAMPLE 3

Induction of phthalyl amidase

Three compounds at different concentrations were added to aerated cultures of the organism growing at 30° C. in Bac MI medium. The compounds tested were phthalate (PAA), phthalyl glycine (PAG), and PMBL. Cells of *Xanthobacter agilis* were grown with aeration for 24 hours. This vegetative culture was used to inoculate Bac MI medium (50 ml) containing different concentrations of the compounds to be tested. After 48 hours growth under standard conditions, cells were harvested by centrifugation and wet weight of the cells was determined. Crude cell extracts were prepared by lysozyme treatment of the cells as in Example 1. Suspensions were briefly sonicated to break up the viscous suspension. A cell-free supernatant was obtained by centrifugation of the suspension at 14,000 rpm for 15 minutes.

Enzyme activity in cell-free lysates was determined by monitoring conversion of the chromogenic substrate 4-(2'-carboxy-N-benzoyl)amino-2-carboxynitrobenzene (II) to 2-nitro-5-amino benzoic acid and phthalic acid, a reaction catalyzed by phthalyl amidase as shown below:

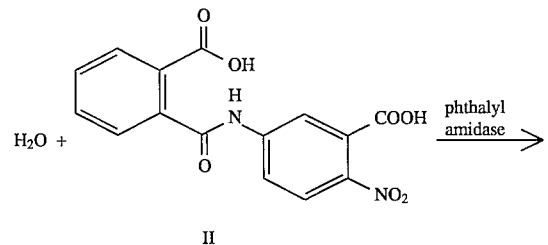

II

-continued

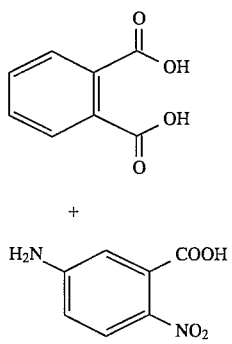

The assay reaction mixture (1 ml) consisted of 0.3 μmol of the chromogenic substrate (II) and 0.001–0.5 μg of enzyme preparation in 50 mM potassium phosphate buffer, pH 8.0 (buffer A). The enzymatic reaction was conducted at 30° C. for 10 minutes and the appearance of product was monitored at 380 nm (or 430 nm). The amount of substrate hydrolyzed was calculated from a standard curve of the amine product.

As can be seen in Table 1, PAG and PAA increased the wet weight cell mass while PMBL had no effect. However, all three substrates produced a dramatic concentration-dependent increase in the total number of enzyme units recovered. The units of enzyme per gram of wet weight cells also increased with all additions but the increase was most pronounced at high PAA concentrations.

TABLE 1

| Inducer | Addition (mg/ml) | Cell weight (g/50 ml) | Total units/ mg protein (μmol/min/mg) | Units/ g cells |
|---|---|---|---|---|
| Control | — | 0.29 | 0.017 | 0.06 |
| PAG | 1 | 0.33 | 0.35 | 1.04 |
|  | 5 | 0.5 | 4.4 | 9.4 |
| PMBL | 1 | 0.35 | 0.28 | 0.79 |
|  | 5 | 0.24 | 2.0 | 8.1 |
| PAA | 1 | 0.35 | 1.4 | 3.9 |
|  | 2 | 0.47 | 4.3 | 9.3 |
|  | 5 | 0.7 | 3.7 | 5.5 |
|  | 10 | 0.6 | 12.0 | 19.8 |

EXAMPLE 4

Purification of phthalyl amidase

A. Analytical scale purification of phthalyl amidase

Cells of *Xanthobacter agilis* (200 grams, wet weight), which contained significant amounts of phthalyl amidase activity, were resuspended to 1800 ml in 50 mM Tris-HCl, pH 8.0, plus 5 mM EDTA. The cells were broken by sonication for 22 minutes at a maximal power below 8° C. DNase (1 μg/ml) and magnesium sulfate (10 mM) were added during the sonication to minimize viscosity and improve cell breakage. After a high-speed centrifugation, the resulting crude extract supernatant served as the source for further enzyme purification. All subsequent purification steps were conducted at 4° C.

The crude extract was loaded onto a Q-Sepharose column (4.4×23 cm; Pharmacia), previously equilibrated with buffer A. After washing with buffer A, a linear gradient of 0–1.5M KCl in buffer A was applied and the phthalyl amidase eluted as a single activity peak between 1 and 1.1M KCl. Selected fractions containing most of the enzyme activity were pooled as Q-Sepharose eluate.

The Q-Sepharose eluate was subjected to ammonium sulfate fractionation. The majority of the enzyme activity was recovered from 67–77, 77–87 and 87–97% ammonium sulfate pellets. Those pellets were solubilized in buffer A with 0.2M ammonium sulfate.

Ammonium sulfate was added to the 67–97% ammonium sulfate enzyme pool to a final concentration of approximately 2M. The enzyme pool was loaded onto a Phenyl-Sepharose column (2.6×16 cm; Pharmacia), which was previously equilibrated with buffer A plus 2.6M ammonium sulfate. The phthalyl amidase eluted with a linear gradient decreasing from 2.6M to 0M ammonium sulfate in buffer A as a single activity peak between 0M and 0.5M ammonium sulfate. Selected fractions containing the majority of the enzyme activity were pooled as Phenyl-Sepharose eluate.

The Phenyl-Sepharose eluate was dialyzed against buffer A and then loaded onto a hydroxylapatite column (1.5×90 cm; Clarkson Chemical Company, Williamsport, Pa.), which was previously equilibrated with buffer A. After washing the column with buffer A, the enzyme eluted with a linear gradient of 50–500 mM potassium phosphate, pH 8.0, as a single activity peak between 150 and 190 mM potassium phosphate. Selected fractions containing most of the enzyme activity were pooled as hydroxylapatite eluate.

After a dilution of the buffer strength from 120 to 50 mM potassium phosphate, the hydroxylapatite eluate was loaded onto a Mono P column (0.5×20 cm; Pharmacia), which was previously equilibrated with buffer A. After washing with 3 column volumes of buffer A, a linear gradient of 0–1.5M KCl in buffer A was applied and the enzyme eluted as a single activity peak between 0.72 and 0.8M KCl. Those fractions containing the majority of the enzyme activity were pooled as Mono P eluate. The most active enzyme preparation was derived from Mono P FPLC (Fast Protein Liquid Chromatography).

Table 2 summarizes the results of the purification. Based on sodium dodecyl sulfate-polyacrylamide gel electrophoresis (SDS-PAGE) and Laser Densitometric Scanning, the phthalyl amidase was greater than 95% pure.

The phthalyl amidase activity reported in Table 2 was determined using the chromogenic substrate as in Example 3. A typical reaction mixture in a total volume of 1 ml contained 0.2 mg of the chromogenic substrate and an aliquot of phthalyl amidase in buffer A. The enzymatic reaction was conducted at 30° C. for 10–15 min. Formation of the reaction product was monitored with a spectrophotometer at 430 nm (or 380 nm) and quantitated from a standard curve of the product.

TABLE 2

| Step | Protein (mg) | Activity (Units) | Spec. Act. (Units/mg) | Purification (fold) | Yield (%) |
|---|---|---|---|---|---|
| Crude Extract | 5475 | 345 | 0.063 | 1 | 100 |
| Q Sepharose | 230 | 279 | 1.214 | 19 | 81 |
| Ammonium Sulfate: 67–97% cut | 145 | 224 | 1.547 | 25 | 65 |
| Phenyl-Sepharose | 63 | 158 | 2.505 | 40 | 46 |
| Hydroxylapatite | 28 | 154 | 5.52 | 88 | 45 |
| Mono P | 16.5 | 119 | 7.2 | 119 | 34 |

B. Preparative scale purification of phthalyl amidase

Crude extract of *Xanthobacter agilis* was prepared by adding 1 g of cells (wet weight) and 2 mg lysozyme per 9 ml of 50 mM Tris-HCl buffer, pH 8.0, 1 mM EDTA (600 g cells total). After 30 minutes at room temperature, DNase (100 U/g of cells) in 10 mM magnesium sulfate was added. The cells were homogenized using a cell homogenizer for 30 minutes at room temperature. After 17 hours of incubation at 8° C., the lysate was centrifuged at 10,000 rpm for 30 minutes.

The crude extract supernatant (4.5 L) was applied to a Super-Q column (7×40 cm; TosoHaas, Montgomeryville, Pa.) equilibrated in buffer A. After loading crude extract, the column was washed with 2 column volumes of 50 mM phosphate buffer containing 3.5M urea, pH 8.0. A second wash (5 L) was used to re-equilibrate the column in buffer A. Phthalyl amidase eluted from the column using a 10 column-volume linear gradient of 0–1.5M KCl in buffer A. Fractions were collected and assayed for enzyme activity. The active fractions were pooled (1.5 L), concentrated (250 ml), and diafiltered with buffer A at 7°–10° C.

The concentrated and diafiltered Super-Q mainstream was applied to a hydroxylapatite column (3.2×40 cm) equilibrated in buffer A. After washing the column with this buffer, phthalyl amidase was eluted using a linear gradient of 0–500 mM phosphate buffer, pH 8.0. Fractions were assayed according to the chromogenic substrate method (see Example 3) and the active fractions were pooled (1 L) and concentrated (400 ml).

Table 3 shows the results of this purification.

TABLE 3

| Step | Activity (Units) | Spec. Act. (Units/mg) | Purification (Fold) | Yield (%) |
| --- | --- | --- | --- | --- |
| Crude Extract | 14,846 | 0.8 | 1 | 100 |
| Super-Q | 6,828 | 3.0 | 4 | 46 |
| Hydroxyl-apatite | 4,985 | 9.0 | 11 | 34 |

EXAMPLE 5

Effect of pH on phthalyl amidase activity

The effect of pH on the reaction rate of the analytical scale purified enzyme was determined using phthalamido carbacephem (III) as substrate.

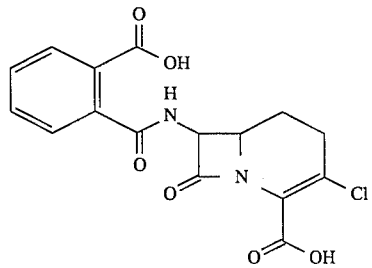

III

A typical reaction mixture consisted of 1 ml total volume and contained 0.1 mM III, 0.1 µM phthalyl amidase in 50 mM potassium phosphate buffer (pH 5.5–9.0) 32° C. for 20 minutes. The reactions were stopped by the addition of 1 ml methanol. After removal of precipitate by centrifugation, an aliquot of the supernatant fraction (typically 30 µl) was monitored for the beta-lactam nucleus and phthalic acid by HPLC using a Zorbax C8 column (0.46×15 cm; MacMod Analytical Inc., Chadds Ford, Pa.). The two reaction products were eluted by a mobile phase constructed as continuous mixed gradients from (a) 1% ACN (acetonitrile)/0.2% TFA (trifluoroacetic acid) and (b) 80% ACN/0.2% TFA as follows: 1) 0% (b), 3 min; 2) 0–50% (b), 0.5 min; 3) 50–100% (b), 3 min; 4) 100% (b), 2.5 min; 5) 100–0% (b), 0.1 min; and 6) 0% (b), 5 min. At a flow rate of 1.5 ml/min, retention times of the beta-lactam nucleus and phthalic acid, as measured at 254 nm, were 2.3 and 7.2 min, respectively.

The results are shown in Table 4. Optimal range for enzyme activity occurred between pH 7.3 and 8.4.

TABLE 4

| pH | Specific Activity (µmol/min/µmol enzyme) |
| --- | --- |
| 7.0 | 125.4 |
| 7.2 | 130.4 |
| 7.4 | 155.2 |
| 7.6 | 172.5 |
| 7.8 | 184.2 |
| 8.0 | 195.3 |
| 8.2 | 201.2 |
| 8.4 | 208.0 |
| 8.6 | 181.7 |
| 8.8 | 185.1 |
| 9.0 | 33.1 |

EXAMPLE 6

Optimum reaction temperature

Test reactions were carried out similar to Example 5 except that all incubations were performed in 50 mM potassium phosphate buffer at pH 8.2. Solutions of the substrate were pre-incubated for 5 minutes at temperatures between 2° and 60° C. The enzymatic reaction was initiated by the addition of phthalyl amidase and stopped by the addition of 1 ml methanol. Specific activity of the enzyme was determined by monitoring the hydrolysis of III by HPLC as in Example 5.

The maximum reaction rate for the enzyme was reached at 34° C. Little enzyme activity was found below 10° C. and above 50° C.

EXAMPLE 7

Optimum salt concentration

Test reactions were carried out similar to Example 6 except that buffer concentrations ranging from 10 to 200 mM at 32° C. were examined. All other conditions and analyses were the same.

As is apparent in Table 5, high salt concentration markedly improved the specific activity of the enzyme. The effect was of a general nature and did not appear to be dependent on specific anions or cations.

TABLE 5

| Buffer Conc. | Specific Activity (µmol/min/µmol enzyme) | | |
| --- | --- | --- | --- |
| (mM) | K Phosphate | Tris-HCl | $NH_4$ Acetate |
| 10 | 148 | 73 | 25 |
| 50 | 300 | 230 | 50 |
| 100 | 350 | 275 | 75 |
| 200 | 360 | 300 | 100 |

EXAMPLE 8

Stability of phthalyl amidase

A. Effect of ionic strength

The stability of phthalyl amidase at pH values ranging from 6–9 was determined as described in Example 5 at 30° C. in both 20 and 200 mM potassium phosphate buffer. In 20 mM buffer, all enzyme activity was lost within 2 hours at any pH of the incubation medium. In 200 mM buffer, the enzyme retained at least 80% of its activity for 100 hours irrespective of the pH of the incubating medium. Twenty mM buffer that was supplemented with 200 mM KCl or NaCl also protected against activity loss, indicating that the enzyme stabilization was primarily dependent on the high ionic strength of the buffer.

B. Temperature stability

The phthalyl amidase enzyme was also tested for stability at varying temperatures. The enzyme was incubated at pH 8.2 in the temperature range of 4°–50° C. for 48 hours in 50 and 200 mM phosphate buffer. In 50 mM buffer, the enzyme retained 90% of its activity for 48 hours when maintained at temperatures below 25° C., while all enzyme activity was lost within 48 hours when the incubation temperature was above 40° C. In 200 mM buffer, 80% of the enzyme activity was retained in temperatures up to 35° C. and 30% of the enzyme activity was retained after 48 hours incubation at 40° C.

EXAMPLE 9

Influence of effectors on enzyme activity

The effect of various agents on the enzymatic activity of phthalyl amidase was determined using standard conditions (see Example 5). All agents were tested at 1 mM final concentration unless otherwise indicated.

It can be seen from the data in Table 6 that iodoacetate, p-HMB, and copper ions significantly reduced phthalyl amidase activity. None of the tested compounds stimulated enzyme activity significantly above that of the control.

Table 7 shows the effects of four organic solvents at three concentrations on enzyme catalysis. All four solvents tested significantly decreased enzyme activity at a concentration of 10%. Glycerol caused the least amount of inhibition of the enzyme at the highest concentration tested.

TABLE 6

| Effector Agent | % of Control Activity |
|---|---|
| Sulfhydryl agents | |
| p-HMB | 65 |
| DTNB | 98 |
| NEM | 100 |
| Iodoacetate, 1 mM | 91 |
| Iodoacetate, 10 mN | 46 |
| Metal chelators | |
| Phenanthroline | 104 |
| EDTA | 103 |
| Co-factors and reducing agents | |
| Mercaptoethanol | 105 |
| DTT | 100 |
| NAD | 101 |
| NADH | 96 |
| NADP | 99 |
| NADPH | 99 |

TABLE 6-continued

| Effector Agent | % of Control Activity |
|---|---|
| ATP | 96 |
| PLP | 106 |
| THF | 100 |
| CoASH | 102 |
| THF + DTT | 100 |
| FAD | 101 |
| FAD + DTT | 100 |
| Metal Cations | |
| NaCl | 104 |
| KCl | 100 |
| $CaCl_2$ | 89 |
| $CoCl_2$ | 101 |
| $CuCl_2$ | 36 |
| $FeCl_2$ | 102 |
| $FeCl_3$ | 96 |
| $MgCl_2$ | 102 |
| $MnCl_2$ | 84 |
| $NiCl_2$ | 94 |
| $ZnCl_2$ | 100 |

DTT: dithiothreitol
p-HMB: para-hydroxy mercuric benzoate
DTNB: dithionitrobenzoate
NEM: N-ethylmaleimide
NAD: nicotinamide adenine nucleotide
NADP: nicotinamide adenine dinucleotide phosphate
NADPH: reduced form of NADP
ATP: adenosine 5'-triphosphate
PLP: pyridoxy-5-phosphate
THF: tetrahydrofolate
FAD: flavin adenine dinucleotide

TABLE 7

| | % Residual enzyme activity | | |
|---|---|---|---|
| Solvent | 1.0% | 5.0% | 10.0% |
| Ethanol | 99 | 85 | 45 |
| DMSO | 101 | 80 | 71 |
| Glycerol | 100 | 94 | 85 |
| Methanol | 100 | 90 | 69 |

DMSO: dimethyl sulfoxide

EXAMPLE 10

Physical and chemical properties of phthalyl amidase

The molecular weight of the phthalyl amidase was determined to be 49,900 by electrospray mass spectrometry. The enzyme is monomeric with an isoelectric point estimated by isoelectric focusing to be pH 5.5. Chemical hydrolysis and amino acid analysis of the protein by standard methods are shown in Table 8. Repeated attempts to sequence the N-terminus of the purified enzyme failed, indicating that the enzyme was blocked.

TABLE 8

| Amino Acid | Number of residues in protein |
|---|---|
| Aspartate/Asparagine | 62 |
| Threonine | 21 |
| Serine | 37 |
| Glutamate/Glutamine | 52 |
| Proline | 26 |
| Glycine | 34 |
| Alanine | 50 |
| Cysteine* | 2 |

TABLE 8-continued

| Amino Acid | Number of residues in protein |
|---|---|
| Valine | 23 |
| Methionine | 12 |
| Isoleucine | 20 |
| Leucine | 35 |
| Tyrosine | 17 |
| Phenylalanine | 13 |
| Histidine | 11 |
| Lysine | 4 |
| Arginine | 20 |
| Tryptophan* | 13 |

*derived from nucleotide sequence of the gene

EXAMPLE 11

Substrate specificity of phthalyl amidase

A. Chemical structure requirements for enzyme activity

The activity of phthalyl amidase against 25 compounds was determined. The compounds were divided into beta-lactams (Table 9), phthalyl amides (Table 10), and aromatic ring substituted amides (Table 11). Each reaction mixture (1 ml total volume) contained 2.5 μmol of compound and 0.3 units of enzyme (based on the chromogenic substrate) of the preparative scale purified enzyme, in 50 mM phosphate buffer, pH 8.0. The reactions were conducted at 30° C. Samples of the reaction mixture were taken at various times, and methanol (equal volume) was added to stop the reaction. The samples were examined by HPLC to determine the extent of substrate hydrolysis. The amount of compound hydrolyzed was calculated from a standard curve of the test compound. All substrates were stable in buffer at 30° C. and pH 8.0 in the absence of enzyme for 24 hours.

As the results in Table 9 indicate, the enzyme recognizes mono- and bicyclic beta-lactam compounds containing a phthalyl group attached to the exocyclic nitrogen. However, the side chain apparently requires a 2-carboxylate group, for example, phthalate, since no hydrolysis is observed in the absence of this functional group.

A wide variety of phthalyl amides are substrates for the enzyme as shown in Table 10. Substrates include phthalylated amino acids, dipeptides, monocyclic and bicyclic beta-lactams, phenyl, benzyl, and aliphatic amines. The enzyme also exhibited esterase activity as demonstrated by its ability to hydrolyze phthalate mono methyl ester (IX). In this series, compound XIII was the most active compound found.

Using compound XIII as a standard, a variety of aromatic ring substituted compounds were examined for reactivity with the enzyme. Results are shown in Table 11. Aromatic ring substituents at the 6 position of the phthalyl ring such as F and $NH_2$ were accepted by the enzyme. A hydroxyl group at the 3 position (XXI) of the ring and a nitrogen within the aromatic ring (XX) is also acceptable. Low levels of hydrolysis occur if a tetrazole is substituted for the 2-carboxylate group (XXII). Moving the carboxylate group to the 3 (XXIV) or 4 (XXIII) position of the aromatic ring completely eliminates hydrolytic activity. Compounds lacking the 2-carboxylate (XXV–XXVIII) are not suitable substrates for the enzyme.

These results are consistent with the enzyme being a novel catalyst that removes phthalyl protecting groups from a variety of amines under mild conditions.

TABLE 9

| Compound number | Structure | Relative activity |
|---|---|---|
| I | [structure] | 47.9 |
| III | [structure] | 100 |

TABLE 9-continued

| Compound number | Structure | Relative activity |
|---|---|---|
| IV | phenoxyacetamide-azetidinone-furan-CH₂COOH derivative | 0 |
| V | phenylacetamide-azetidinone-furan-CH₂COOH derivative | 0 |
| VI | benzamide-azetidinone-furan-CH₂COOH derivative | 0 |

TABLE 10

2-substituted benzoic acid core structure with R group

| Compound number | R Group | Relative Activity |
|---|---|---|
| II | NH-(4-COOH-2-NO₂-phenyl) | 295.7 |
| III | 3-chloro-carbacephem amino group | 100.0 |
| VIII | NH-(4-NO₂-phenyl) | 544.6 |
| IX | —OCH₃ | 207.6 |
| X | NH-benzyl | 40.2 |

TABLE 10-continued

[Structure: phthalic acid derivative with R group on one carbonyl]

| Compound number | R Group | Relative Activity |
|---|---|---|
| XI | -NH-CH₂-COOH (glycine) | 31.8 |
| XII | -NH-CH(CH₃)₂ (isopropyl) | 9.7 |
| XIII | -NH-CH(imidazolyl-CH₂)-(CH₂)₅CH₃-COOH | 1027.2 |
| XIV | -L-Asp-L-Phe—OMe | 118.5 |
| XV | -D,L-methionine | 220.1 |
| XVI | -D,L-leucine | 90.2 |

TABLE 11

[Structure: substituted benzamide with R on phenyl ring positions 3-6, attached to imidazolyl-heptyl carboxylic acid]

| Compound number | R Group | Relative Activity |
|---|---|---|
| XVII | 2-COOH | 100.0 |
| XVIII | 6-F, 2-COOH | 159.00 |
| XVIX | 6-NH₂, 2-COOH | 10.2 |
| XX | 2-COOH (with N at position 6) | 85.9 |
| XXI | 3-OH, 2-COOH | 1.3 |
| XXII | [tetrazole-NH group] at position 2 | 0.2 |
| XXIII | 4-COOH | 0 |
| XXIV | 3-COOH | 0 |
| XXV | 2-OH | 0 |
| XXVI | 3-OH | 0 |
| XXVII | 3,5-OH | 0 |
| XXVIII | 2-H | 0 |

B. Kinetic parameters for phthalyl amidase

The kinetic parameters of the enzyme were determined for several representative substrates. Compounds II, XVII, and XVIII were tested using 0.9 μg/ml of enzyme. Compounds III and XI were tested using 5.14 μg/ml of enzyme. Substrate concentrations were between 0 and 25 mM and reaction time was between 2 and 20 minutes, depending on the substrate used. All reactions were run at 32° C. and at pH 8.2. The $K_m$, $V_{max}$, $K_{cat}$, and $K_{cat}/K_m$ for these substrates are shown in Table 12. $K_m$ is the Michaelis constant for enzyme kinetics, $V_{max}$ is the maximal rate of reaction calculated by the Michaelis-Menten equation, and $K_{cat}$ is the catalytic constant for an enzyme reaction.

TABLE 12

| Parameter | Substrate | | | | |
| --- | --- | --- | --- | --- | --- |
|  | II | III[a] | XI | XVII | XVIII[b] |
| $K_m$ (mM) | 0.05 | 0.9 | 0.14 | 0.09 | 0.17 |
| $V_{max}$ (μmol/min/mg) | 5.95 | 7.6 | 0.27 | 1.41 | 1.94 |
| $K_{cat}$ (μmol/sec/μmol) | 4.95 | 6.33 | 0.22 | 1.18 | 1.61 |
| $K_{cat}/K_m$ | 99.0 | 7.0 | 1.6 | 13.1 | 9.5 |

[a]carbacepham nucleus (7-amino-3-chloro-4-carboxy-1-carba-dethioceph-3-em) (XXXIV) quantitatively monitored as the product of substrate III.
[b]for the other substrates, phthalic acid was the product monitored during the reaction.

C. Chiral and additional substrate selectivity of phthalyl amidase.

Several additional substrates were tested in a total volume of 1 ml. Reaction mixtures contained 0.009 mg (0.6 units) of enzyme, 2.5 μmol of substrate, and buffer A. All reactions were run at 30° C. for 2 minutes except for compounds XXX and XXXII, which were run for a longer time period since they were poor substrates for the enzyme. Reactions were stopped by the addition of methanol, and phthalic acid formation was monitored by HPLC. Results are shown in Table 13.

The results show that the enzyme has a marked preference for the D isomer of N-phthalyl-phenylglycine. The L isomer was an extremely poor substrate for the enzyme. Compound XXXI had a relative activity twice that of compound III as a substrate for the enzyme. However, by substituting a sulfonate group for the carboxyl group of the phthalyl moiety, enzyme reactivity is completely lost. Again, these results show the selectivity of this enzyme for N-phthalylated amines and indicate that the enzyme has a chiral preference on the amine side of the substrate.

TABLE 13

| Compound Number | Structure | Relative Activity |
|---|---|---|
| III | (phthalamido carbacephem structure with COOH, NH, C=O, N, Cl, COOH) | 100 |
| XVIX | (D-isomer: benzene-COOH, C(=O)NH-CH(Ph)-COOH) D-isomer | 136 |
| XXX | (L-isomer: benzene-COOH, C(=O)NH-CH(Ph)-COOH) L-isomer | 1.3 |
| XXXI | (benzene-COOH, C(=O)NH-Ph) | 200 |
| XXXII | (benzene-SO₃K, C(=O)NH-Ph) | 0.0 |

EXAMPLE 12

Preparative scale synthesis of carbacephem nucleus

Phthalimido carbacephem (XXXIII) readily hydrolyzes to phthalamido carbacephem (III) in buffer at pH 8.0. Thus, either compound XXXIII or III can be used to prepare the carbacephem nucleus (XXXIV). Substrate (4 grams) was added to 20 ml of deionized water and the pH of the solution was adjusted to 8.0 with concentrated ammonium hydroxide. Phthalyl amidase, 80 units as determined using the chromogenic substrate (II), was added to start the reaction. Temperature was maintained at 30° C. and the pH maintained at 8.0 by adding 2N ammonium hydroxide. After 510 minutes under these conditions, HPLC analysis of the samples from the reaction indicated that compound III was 90.0% hydrolyzed and compound XXXIII was 98% hydrolyzed. The pH of the reaction was lowered to 5.0 thereby precipitating the carbacephem nucleus. Isolated yields of the nucleus were between 65% and 77%.

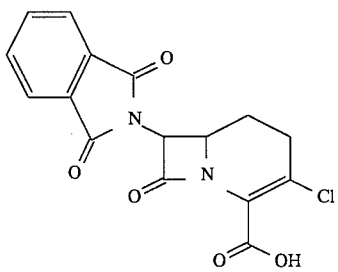

XXXIII

-continued

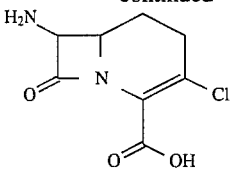
XXXIV

EXAMPLE 13

Expression of met-phthalyl amidase in *Escherichia coli*

Several small scale temperature inductions of *E. coli* DH5α/pZPA400 were carried out to assess the amount of met-phthalyl amidase protein and enzymatic activity generated by *E. coli* DH5α/pZPA400. Enzymatic activity was observed by incubation of a soluble cell extract with the chromogenic substrate (II) under conditions as described in Example 3 or with substrate III as described in Example 5. Results are reported in Table 14.

SDS-PAGE gels of the cell extract showed a Coomassie-stained protein band corresponding to approximately 50,000 daltons that increased upon temperature induction. Partial purification of the cell extract by anion exchange chromatography yielded fractions with increased phthalyl amidase specific activity. Phthalyl amidase in these fractions catalyzed cleavage of the phthalyl group from compound III to form compound XXXIV and phthalic acid.

EXAMPLE 14

Expression of pro-phthalyl amidase open reading frame in *Streptomyces lividans*

A 5 ml inoculum of *Streptomyces lividans* TK23/pZPA600 (grown for 48 hours at 30° C., 280 rpm) was added to each of two 2 L shake flasks containing 500 ml Trypticase Soy Broth medium and cultured at 30° C., 280 rpm for 24 hours. Incubations beyond 24 hours were deleterious to production of phthalyl amidase. Cells were removed by centrifugation (4° C., 15 min, 12,000×g) and phthalyl amidase activity in the cell-free broth was determined with compound III as substrate as in Example 13 (Table 14). The cell-free broth (800 ml, 0.10 mg/ml) was passed at 1 ml/min through a Mono Q column (10×10 mm (8 ml); Pharmacia). A linear gradient of 0 to 1.5M KCl in buffer A was passed over the column and 2 ml fractions were collected. Most of the phthalyl amidase activity eluted in fractions 19 and 20 (about 0.75M KCl).

A 1 ml aliquot of fraction 19 was concentrated 10-fold via ultrafiltration and analyzed by SDS-PAGE. A major protein band was observed at about 50,000 daltons, which corresponded to the molecular weight observed by electrospray mass spectrometry for purified mature phthalyl amidase obtained from *Xanthobacter agilis*. It also corresponded closely to the theoretical molecular weight predicted for a protein encoded by SEQ ID NO:1.

TABLE 14

| Expressing Organis | Plasmid | Specific Activity (nmol/min/mg) | Volumetric Activity (nmol/min/L) |
|---|---|---|---|
| *Xanthobacter agilis* | none | 63.0[a] | 3465[a] |
| *Escherichia coli* | pZPA400 | 0.96[b] | 438[b] |
| *Streptomyces lividans* | pZPA600 | 748.8[b] | 76,378[b] |

Specific activity - units of enzyme/mg total protein
Volumetric activity - units of enzyme/liter of whole broth
Unit of enzme - amount of enzyme that converts one nanomole of substrate in one minute
Phthalyl amidase is cell-bound for both *Xanthobacter agilis* and *Escherichia coli*; for *Streptomyces lividans* phthalyl amidase is secreted into the culture medium.
[a]Method of release by sonication as in Example 4A. See also Example 4B where method of release by lysozyme treatment.
[b]Method of assay as in Example 5.

EXAMPLE 15

Use of recombinant phthalyl amidase to remove the phthalyl blocking group from phthalamido carbacephem Activity was assayed by the addition of phthalyl amidase (30 μl of Mono Q fraction 19 from Example 14, 1.83 μg total protein) to 1.82 μg of compound III in a 1 ml reaction mixture buffered by 200 mM potassium phosphate, pH 8.2. The reaction was carried out at 32° C. for 20 minutes and stopped with the addition of 1 ml methanol. After removal of precipitate by centrifugation, an aliquot (30 μl) of the supernatant fraction was monitored by HPLC (254 nm absorbance) for both the carbacephem nucleus (XXXIV) and phthalic acid using a Zorbax C8 column (0.46×15 cm; MacMod Analytical Inc.). The reaction products were eluted by a mobile phase constructed as continuous mixed gradients from (a) 1% acetonitrile/0.2% trifluoroacetic acid and (b) 80% acetonitrile/0.2% trifluoroacetic acid. The above substrate, loracarbef nucleus, and phthalic acid eluted at 11.0, 3.4, and 5.9 minutes, respectively. HPLC peaks were identified and quantitated using data generated by known amounts of authentic compounds. The specific activity of recombinant phthalyl amidase derived from fraction 19 for conversion of substrate was 9.5 μmol/min/mg protein.

EXAMPLE 16

Use of recombinant phthalyl amidase to remove the phthalyl blocking group from phthalimido-aspartame In the synthesis of aspartame, the bivalent protection of the amino group of L-aspartic acid via a phthalimido moiety gives a superior substrate for a lyase- condensation with L-phenylalanine methyl ester. However, an efficient method to convert the phthalimido-protected compound back to the amine was previously lacking. Following the condensation reaction, mild base was used to open the phthalimido moiety to a phthalamido moiety and recombinant phthalyl amidase was then used to catalyze hydrolysis of the latter to aspartame and phthalic acid (see Table 10).

We claim:

1. A DNA compound that comprises an isolated nucleotide sequence which is SEQ ID NO: 7.

2. A DNA compound that comprises an isolated nucleotide sequence encoding SEQ ID NO: 9.

3. The DNA compound of claim 2 wherein said isolated nucleotide sequence is SEQ ID NO: 8.

4. An isolated amino acid sequence according to SEQ ID NO: 9.

* * * * *

UNITED STATES PATENT AND TRADEMARK OFFICE
CERTIFICATE OF CORRECTION

PATENT NO. : 5,543,497

DATED : August 6, 1996

INVENTOR(S) : Stephen W. Queener, et al.

It is certified that error appears in the above-identified patent and that said Letters Patent is hereby corrected as shown below:

Column 2, Line 1, "SWQ" should be --SEQ--
Column 2, Line 66, "2-ene" should be deleted (second occurrence)
Column 14, Line 9, "7.3" should be --7.8--

Signed and Sealed this

Twenty-sixth Day of May, 1998

Attest:

BRUCE LEHMAN

Attesting Officer                Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1359 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1356

( x i ) SEQUENCE DESCRIPTION: SEQ ID NO:1:

```
CAG  GCG  CCG  TCT  GTG  CAC  CAA  CAC  GTC  GCC  TTC  ACT  GAG  GAA  ATT  GGA      48
Gln  Ala  Pro  Ser  Val  His  Gln  His  Val  Ala  Phe  Thr  Glu  Glu  Ile  Gly
 1              5                   10                  15

GAC  CTT  CCC  GAC  GGC  TCA  AGT  TAC  ATG  ATC  CGT  GTG  CCG  GAG  AAC  TGG      96
Asp  Leu  Pro  Asp  Gly  Ser  Ser  Tyr  Met  Ile  Arg  Val  Pro  Glu  Asn  Trp
                20                  25                  30

AAC  GGC  GTG  TTA  ATT  CGC  GAC  CTA  GAC  CTT  GTC  AGC  GGC  ACC  AGC  AAT     144
Asn  Gly  Val  Leu  Ile  Arg  Asp  Leu  Asp  Leu  Val  Ser  Gly  Thr  Ser  Asn
         35                   40                  45

TCT  AAC  GCC  GCA  AGG  TAC  GAA  ACC  ATG  CTG  AAA  GAA  GGT  TTT  GCC  GTT     192
Ser  Asn  Ala  Ala  Arg  Tyr  Glu  Thr  Met  Leu  Lys  Glu  Gly  Phe  Ala  Val
         50                   55                  60

GCT  GGC  ACG  GCG  AGG  CAT  CCC  CTT  CGG  CAA  TGG  CAA  TAT  GAC  CCC  GCT     240
Ala  Gly  Thr  Ala  Arg  His  Pro  Leu  Arg  Gln  Trp  Gln  Tyr  Asp  Pro  Ala
65                   70                  75                  80

CAC  GAG  ATT  GAA  AAC  CTC  AAT  CAC  GTG  CTG  GAC  ACA  TTC  GAG  GAA  AAT     288
His  Glu  Ile  Glu  Asn  Leu  Asn  His  Val  Leu  Asp  Thr  Phe  Glu  Glu  Asn
                85                  90                  95

TAC  GGT  TCA  CCT  GAA  AGA  GTT  ATC  CAG  TAC  GGT  TGC  TCG  GGT  GGG  GCA     336
Tyr  Gly  Ser  Pro  Glu  Arg  Val  Ile  Gln  Tyr  Gly  Cys  Ser  Gly  Gly  Ala
                100                 105                 110

CAC  GTG  TCA  CTA  GCC  GTG  GCA  GAG  GAC  TTC  TCG  GAC  CGC  GTA  GAT  GGC     384
His  Val  Ser  Leu  Ala  Val  Ala  Glu  Asp  Phe  Ser  Asp  Arg  Val  Asp  Gly
         115                 120                 125

TCA  GTT  GCT  CTA  GCT  GCT  CAT  ACT  CCT  GTC  TGG  ATA  ATG  AAT  TCT  TTC     432
Ser  Val  Ala  Leu  Ala  Ala  His  Thr  Pro  Val  Trp  Ile  Met  Asn  Ser  Phe
         130                 135                 140

TTG  GAC  GGA  TGG  TTT  TCG  CTG  CAG  TCT  CTG  ATC  GGC  GAG  TAC  TAT  GTA     480
Leu  Asp  Gly  Trp  Phe  Ser  Leu  Gln  Ser  Leu  Ile  Gly  Glu  Tyr  Tyr  Val
145                 150                 155                 160

GAA  GCT  GGT  CAC  GGC  CCA  CTT  TCG  GAT  CTC  GCT  ATT  ACG  AAA  CTG  CCC     528
Glu  Ala  Gly  His  Gly  Pro  Leu  Ser  Asp  Leu  Ala  Ile  Thr  Lys  Leu  Pro
                165                 170                 175

AAT  GAT  GGT  AGC  TCT  AAT  TCG  AGC  GGT  CAT  GGA  ATG  GAA  GGA  GAT  CTT     576
Asn  Asp  Gly  Ser  Ser  Asn  Ser  Ser  Gly  His  Gly  Met  Glu  Gly  Asp  Leu
                180                 185                 190

CCT  GCC  GCG  TGG  CGC  AAC  GCG  TTC  ACC  GCT  GCT  AAC  GCC  ACA  CCT  GAG     624
Pro  Ala  Ala  Trp  Arg  Asn  Ala  Phe  Thr  Ala  Ala  Asn  Ala  Thr  Pro  Glu
         195                 200                 205

GGT  CGC  GCA  CGC  ATG  GCA  CTA  GCC  TTT  GCG  CTC  GGT  CAG  TGG  TCT  CCG     672
Gly  Arg  Ala  Arg  Met  Ala  Leu  Ala  Phe  Ala  Leu  Gly  Gln  Trp  Ser  Pro
         210                 215                 220
```

| | | | | | | | | | | | | | | | | |
|---|---|---|---|---|---|---|---|---|---|---|---|---|---|---|---|---|
| TGG | TTG | GCC | GAC | AAC | ACG | CCC | CAA | CCT | GAT | CTC | GAT | GAT | CCT | GAG | GCC | 720 |
| Trp 225 | Leu | Ala | Asp | Asn | Thr 230 | Pro | Gln | Pro | Asp | Leu 235 | Asp | Asp | Pro | Glu | Ala 240 | |
| ATC | GCG | GAT | TCC | GTA | TAT | GAG | TCT | GCC | ATG | CGA | CTT | GCA | GGA | AGC | CCT | 768 |
| Ile | Ala | Asp | Ser | Val 245 | Tyr | Glu | Ser | Ala | Met 250 | Arg | Leu | Ala | Gly | Ser 255 | Pro | |
| GGG | GGA | GAA | GCG | CGC | ATA | ATG | TTC | GAG | AAC | GCC | GCT | CGA | GGG | CAA | CAG | 816 |
| Gly | Gly | Glu | Ala 260 | Arg | Ile | Met | Phe | Glu 265 | Asn | Ala | Ala | Arg | Gly 270 | Gln | Gln | |
| CTC | TCT | TGG | AAC | GAC | GAC | ATC | GAC | TAT | GCG | GAT | TTC | TGG | GAG | AAC | TCA | 864 |
| Leu | Ser | Trp 275 | Asn | Asp | Asp | Ile | Asp 280 | Tyr | Ala | Asp | Phe | Trp 285 | Glu | Asn | Ser | |
| AAC | CCA | GCC | ATG | AAG | AGC | GCC | GTT | CAG | GAG | CTG | TAC | GAC | ACG | GCC | GGC | 912 |
| Asn | Pro 290 | Ala | Met | Lys | Ser | Ala 295 | Val | Gln | Glu | Leu | Tyr 300 | Asp | Thr | Ala | Gly | |
| CTT | GAT | CTG | CAG | TCC | GAT | ATA | GAA | ACG | GTA | AAT | TCC | CAG | CCA | CGC | ATA | 960 |
| Leu 305 | Asp | Leu | Gln | Ser | Asp 310 | Ile | Glu | Thr | Val | Asn 315 | Ser | Gln | Pro | Arg | Ile 320 | |
| GAG | GCA | TCG | CAG | TAT | GCG | CTC | GAC | TAC | TGG | AAC | ACG | CCA | GGT | CGC | AAT | 1008 |
| Glu | Ala | Ser | Gln | Tyr 325 | Ala | Leu | Asp | Tyr | Trp 330 | Asn | Thr | Pro | Gly | Arg 335 | Asn | |
| GTC | ATT | GGC | GAC | CCC | GAA | GTT | CCT | GTG | CTG | CGC | CTG | CAT | ATG | ATA | GGC | 1056 |
| Val | Ile | Gly | Asp 340 | Pro | Glu | Val | Pro 345 | Val | Leu | Arg | Leu | His 350 | Met | Ile | Gly | |
| GAC | TAC | CAA | ATT | CCC | TAT | AGT | CTT | GTA | CAG | GGC | TAC | AGC | GAT | CTT | ATC | 1104 |
| Asp | Tyr | Gln 355 | Ile | Pro | Tyr | Ser | Leu 360 | Val | Gln | Gly | Tyr | Ser 365 | Asp | Leu | Ile | |
| TCA | GAG | AAC | AAC | AAT | GAT | GAC | TTG | TAC | AGA | ACT | GCT | TTT | GTG | CAA | TCC | 1152 |
| Ser | Glu 370 | Asn | Asn | Asn | Asp | Asp 375 | Leu | Tyr | Arg | Thr | Ala 380 | Phe | Val | Gln | Ser | |
| ACT | GGA | CAC | TGC | AAT | TTC | ACA | GCT | GCA | GAA | AGT | TCC | GCT | GCG | ATT | GAG | 1200 |
| Thr 385 | Gly | His | Cys | Asn | Phe 390 | Thr | Ala | Ala | Glu | Ser 395 | Ser | Ala | Ala | Ile | Glu 400 | |
| GTC | ATG | ATG | CAA | CGG | CTT | GAC | ACG | GGT | GAG | TGG | CCG | AGC | ACC | GAG | CCG | 1248 |
| Val | Met | Met | Gln | Arg 405 | Leu | Asp | Thr | Gly | Glu 410 | Trp | Pro | Ser | Thr | Glu 415 | Pro | |
| GAT | GAT | CTG | AAT | GCA | ATT | GCC | GAA | GCC | TCA | AAC | ACC | GGA | ACT | GAA | GCA | 1296 |
| Asp | Asp | Leu | Asn 420 | Ala | Ile | Ala | Glu | Ala 425 | Ser | Asn | Thr | Gly | Thr 430 | Glu | Ala | |
| CGT | TTC | ATG | GCC | CTA | GAT | GGC | TGG | GAA | ATA | CCC | GAG | TAC | AAT | CGT | ACT | 1344 |
| Arg | Phe | Met 435 | Ala | Leu | Asp | Gly | Trp 440 | Glu | Ile | Pro | Glu | Tyr 445 | Asn | Arg | Thr | |
| TGG | AAG | CCT | GAA | TAA | | | | | | | | | | | | 1359 |
| Trp | Lys | Pro | Glu 450 | | | | | | | | | | | | | |

( 2 ) INFORMATION FOR SEQ ID NO:2:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Gln 1 | Ala | Pro | Ser | Val 5 | His | Gln | His | Val | Ala 10 | Phe | Thr | Glu | Glu | Ile 15 | Gly |
| Asp | Leu | Pro | Asp 20 | Gly | Ser | Ser | Tyr | Met 25 | Ile | Arg | Val | Pro | Glu 30 | Asn | Trp |
| Asn | Gly | Val | Leu 35 | Ile | Arg | Asp | Leu | Asp 40 | Leu | Val | Ser | Gly | Thr 45 | Ser | Asn |

```
Ser Asn Ala Ala Arg Tyr Glu Thr Met Leu Lys Glu Gly Phe Ala Val
    50                  55                  60
Ala Gly Thr Ala Arg His Pro Leu Arg Gln Trp Gln Tyr Asp Pro Ala
65                  70                  75                   80
His Glu Ile Glu Asn Leu Asn His Val Leu Asp Thr Phe Glu Glu Asn
                85                  90                  95
Tyr Gly Ser Pro Glu Arg Val Ile Gln Tyr Gly Cys Ser Gly Gly Ala
            100                 105                 110
His Val Ser Leu Ala Val Ala Glu Asp Phe Ser Asp Arg Val Asp Gly
        115                 120                 125
Ser Val Ala Leu Ala Ala His Thr Pro Val Trp Ile Met Asn Ser Phe
    130                 135                 140
Leu Asp Gly Trp Phe Ser Leu Gln Ser Leu Ile Gly Glu Tyr Tyr Val
145                 150                 155                 160
Glu Ala Gly His Gly Pro Leu Ser Asp Leu Ala Ile Thr Lys Leu Pro
                165                 170                 175
Asn Asp Gly Ser Ser Asn Ser Ser Gly His Gly Met Glu Gly Asp Leu
            180                 185                 190
Pro Ala Ala Trp Arg Asn Ala Phe Thr Ala Ala Asn Ala Thr Pro Glu
        195                 200                 205
Gly Arg Ala Arg Met Ala Leu Ala Phe Ala Leu Gly Gln Trp Ser Pro
    210                 215                 220
Trp Leu Ala Asp Asn Thr Pro Gln Pro Asp Leu Asp Asp Pro Glu Ala
225                 230                 235                 240
Ile Ala Asp Ser Val Tyr Glu Ser Ala Met Arg Leu Ala Gly Ser Pro
                245                 250                 255
Gly Gly Glu Ala Arg Ile Met Phe Glu Asn Ala Ala Arg Gly Gln Gln
            260                 265                 270
Leu Ser Trp Asn Asp Asp Ile Asp Tyr Ala Asp Phe Trp Glu Asn Ser
        275                 280                 285
Asn Pro Ala Met Lys Ser Ala Val Gln Glu Leu Tyr Asp Thr Ala Gly
    290                 295                 300
Leu Asp Leu Gln Ser Asp Ile Glu Thr Val Asn Ser Gln Pro Arg Ile
305                 310                 315                 320
Glu Ala Ser Gln Tyr Ala Leu Asp Tyr Trp Asn Thr Pro Gly Arg Asn
                325                 330                 335
Val Ile Gly Asp Pro Glu Val Pro Val Leu Arg Leu His Met Ile Gly
            340                 345                 350
Asp Tyr Gln Ile Pro Tyr Ser Leu Val Gln Gly Tyr Ser Asp Leu Ile
        355                 360                 365
Ser Glu Asn Asn Asn Asp Asp Leu Tyr Arg Thr Ala Phe Val Gln Ser
    370                 375                 380
Thr Gly His Cys Asn Phe Thr Ala Ala Glu Ser Ser Ala Ala Ile Glu
385                 390                 395                 400
Val Met Met Gln Arg Leu Asp Thr Gly Glu Trp Pro Ser Thr Glu Pro
                405                 410                 415
Asp Asp Leu Asn Ala Ile Ala Glu Ala Ser Asn Thr Gly Thr Glu Ala
            420                 425                 430
Arg Phe Met Ala Leu Asp Gly Trp Glu Ile Pro Glu Tyr Asn Arg Thr
        435                 440                 445
Trp Lys Pro Glu
    450
```

(2) INFORMATION FOR SEQ ID NO:3:

(i) SEQUENCE CHARACTERISTICS:
        (A) LENGTH: 1485 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1482

(xi) SEQUENCE DESCRIPTION: SEQ ID NO:3:

```
ATG ATA ATC AAG GGT AGT GTA CCG GGT AAA GCC GGA GGA AAA CCT CGA      48
Met Ile Ile Lys Gly Ser Val Pro Gly Lys Ala Gly Gly Lys Pro Arg
 1               5                  10                  15

GCG ACC ATC TTT CAT AGT TCT ATT GCA ACG CTA CTT TTA ACC ACA GTC      96
Ala Thr Ile Phe His Ser Ser Ile Ala Thr Leu Leu Leu Thr Thr Val
                20                  25                  30

TCA CTG TCA GGA GTA GCG CCA GCA TTT GCA CAG GCG CCG TCT GTG CAC     144
Ser Leu Ser Gly Val Ala Pro Ala Phe Ala Gln Ala Pro Ser Val His
                35                  40                  45

CAA CAC GTC GCC TTC ACT GAG GAA ATT GGA GAC CTT CCC GAC GGC TCA     192
Gln His Val Ala Phe Thr Glu Glu Ile Gly Asp Leu Pro Asp Gly Ser
        50                  55                  60

AGT TAC ATG ATC CGT GTG CCG GAG AAC TGG AAC GGC GTG TTA ATT CGC     240
Ser Tyr Met Ile Arg Val Pro Glu Asn Trp Asn Gly Val Leu Ile Arg
 65                 70                  75                  80

GAC CTA GAC CTT GTC AGC GGC ACC AGC AAT TCT AAC GCC GCA AGG TAC     288
Asp Leu Asp Leu Val Ser Gly Thr Ser Asn Ser Asn Ala Ala Arg Tyr
                85                  90                  95

GAA ACC ATG CTG AAA GAA GGT TTT GCC GTT GCT GGC ACG GCG AGG CAT     336
Glu Thr Met Leu Lys Glu Gly Phe Ala Val Ala Gly Thr Ala Arg His
                100                 105                 110

CCC CTT CGG CAA TGG CAA TAT GAC CCC GCT CAC GAG ATT GAA AAC CTC     384
Pro Leu Arg Gln Trp Gln Tyr Asp Pro Ala His Glu Ile Glu Asn Leu
        115                 120                 125

AAT CAC GTG CTG GAC ACA TTC GAG GAA AAT TAC GGT TCA CCT GAA AGA     432
Asn His Val Leu Asp Thr Phe Glu Glu Asn Tyr Gly Ser Pro Glu Arg
130                 135                 140

GTT ATC CAG TAC GGT TGC TCG GGT GGG GCA CAC GTG TCA CTA GCC GTG     480
Val Ile Gln Tyr Gly Cys Ser Gly Gly Ala His Val Ser Leu Ala Val
145                 150                 155                 160

GCA GAG GAC TTC TCG GAC CGC GTA GAT GGC TCA GTT GCT CTA GCT GCT     528
Ala Glu Asp Phe Ser Asp Arg Val Asp Gly Ser Val Ala Leu Ala Ala
                165                 170                 175

CAT ACT CCT GTC TGG ATA ATG AAT TCT TTC TTG GAC GGA TGG TTT TCG     576
His Thr Pro Val Trp Ile Met Asn Ser Phe Leu Asp Gly Trp Phe Ser
                180                 185                 190

CTG CAG TCT CTG ATC GGC GAG TAC TAT GTA GAA GCT GGT CAC GGC CCA     624
Leu Gln Ser Leu Ile Gly Glu Tyr Tyr Val Glu Ala Gly His Gly Pro
        195                 200                 205

CTT TCG GAT CTC GCT ATT ACG AAA CTG CCC AAT GAT GGT AGC TCT AAT     672
Leu Ser Asp Leu Ala Ile Thr Lys Leu Pro Asn Asp Gly Ser Ser Asn
210                 215                 220

TCG AGC GGT CAT GGA ATG GAA GGA GAT CTT CCT GCC GCG TGG CGC AAC     720
Ser Ser Gly His Gly Met Glu Gly Asp Leu Pro Ala Ala Trp Arg Asn
225                 230                 235                 240

GCG TTC ACC GCT GCT AAC GCC ACA CCT GAG GGT CGC GCA CGC ATG GCA     768
Ala Phe Thr Ala Ala Asn Ala Thr Pro Glu Gly Arg Ala Arg Met Ala
                245                 250                 255
```

| | | | | | | | | | | | | | | | | |
|---|---|---|---|---|---|---|---|---|---|---|---|---|---|---|---|---|
| CTA | GCC | TTT | GCG | CTC | GGT | CAG | TGG | TCT | CCG | TGG | TTG | GCC | GAC | AAC | ACG | 816 |
| Leu | Ala | Phe | Ala | Leu | Gly | Gln | Trp | Ser | Pro | Trp | Leu | Ala | Asp | Asn | Thr | |
| | | | 260 | | | | | 265 | | | | | 270 | | | |
| CCC | CAA | CCT | GAT | CTC | GAT | GAT | CCT | GAG | GCC | ATC | GCG | GAT | TCC | GTA | TAT | 864 |
| Pro | Gln | Pro | Asp | Leu | Asp | Asp | Pro | Glu | Ala | Ile | Ala | Asp | Ser | Val | Tyr | |
| | | 275 | | | | | 280 | | | | | 285 | | | | |
| GAG | TCT | GCC | ATG | CGA | CTT | GCA | GGA | AGC | CCT | GGG | GGA | GAA | GCG | CGC | ATA | 912 |
| Glu | Ser | Ala | Met | Arg | Leu | Ala | Gly | Ser | Pro | Gly | Gly | Glu | Ala | Arg | Ile | |
| | 290 | | | | | 295 | | | | | 300 | | | | | |
| ATG | TTC | GAG | AAC | GCC | GCT | CGA | GGG | CAA | CAG | CTC | TCT | TGG | AAC | GAC | GAC | 960 |
| Met | Phe | Glu | Asn | Ala | Ala | Arg | Gly | Gln | Gln | Leu | Ser | Trp | Asn | Asp | Asp | |
| 305 | | | | | 310 | | | | | 315 | | | | | 320 | |
| ATC | GAC | TAT | GCG | GAT | TTC | TGG | GAG | AAC | TCA | AAC | CCA | GCC | ATG | AAG | AGC | 1008 |
| Ile | Asp | Tyr | Ala | Asp | Phe | Trp | Glu | Asn | Ser | Asn | Pro | Ala | Met | Lys | Ser | |
| | | | | 325 | | | | | 330 | | | | | 335 | | |
| GCC | GTT | CAG | GAG | CTG | TAC | GAC | ACG | GCC | GGC | CTT | GAT | CTG | CAG | TCC | GAT | 1056 |
| Ala | Val | Gln | Glu | Leu | Tyr | Asp | Thr | Ala | Gly | Leu | Asp | Leu | Gln | Ser | Asp | |
| | | | 340 | | | | | 345 | | | | | 350 | | | |
| ATA | GAA | ACG | GTA | AAT | TCC | CAG | CCA | CGC | ATA | GAG | GCA | TCG | CAG | TAT | GCG | 1104 |
| Ile | Glu | Thr | Val | Asn | Ser | Gln | Pro | Arg | Ile | Glu | Ala | Ser | Gln | Tyr | Ala | |
| | | 355 | | | | | 360 | | | | | 365 | | | | |
| CTC | GAC | TAC | TGG | AAC | ACG | CCA | GGT | CGC | AAT | GTC | ATT | GGC | GAC | CCC | GAA | 1152 |
| Leu | Asp | Tyr | Trp | Asn | Thr | Pro | Gly | Arg | Asn | Val | Ile | Gly | Asp | Pro | Glu | |
| | 370 | | | | | 375 | | | | | 380 | | | | | |
| GTT | CCT | GTG | CTG | CGC | CTG | CAT | ATG | ATA | GGC | GAC | TAC | CAA | ATT | CCC | TAT | 1200 |
| Val | Pro | Val | Leu | Arg | Leu | His | Met | Ile | Gly | Asp | Tyr | Gln | Ile | Pro | Tyr | |
| 385 | | | | | 390 | | | | | 395 | | | | | 400 | |
| AGT | CTT | GTA | CAG | GGC | TAC | AGC | GAT | CTT | ATC | TCA | GAG | AAC | AAC | AAT | GAT | 1248 |
| Ser | Leu | Val | Gln | Gly | Tyr | Ser | Asp | Leu | Ile | Ser | Glu | Asn | Asn | Asn | Asp | |
| | | | | 405 | | | | | 410 | | | | | 415 | | |
| GAC | TTG | TAC | AGA | ACT | GCT | TTT | GTG | CAA | TCC | ACT | GGA | CAC | TGC | AAT | TTC | 1296 |
| Asp | Leu | Tyr | Arg | Thr | Ala | Phe | Val | Gln | Ser | Thr | Gly | His | Cys | Asn | Phe | |
| | | | 420 | | | | | 425 | | | | | 430 | | | |
| ACA | GCT | GCA | GAA | AGT | TCC | GCT | GCG | ATT | GAG | GTC | ATG | ATG | CAA | CGG | CTT | 1344 |
| Thr | Ala | Ala | Glu | Ser | Ser | Ala | Ala | Ile | Glu | Val | Met | Met | Gln | Arg | Leu | |
| | | 435 | | | | | 440 | | | | | 445 | | | | |
| GAC | ACG | GGT | GAG | TGG | CCG | AGC | ACC | GAG | CCG | GAT | GAT | CTG | AAT | GCA | ATT | 1392 |
| Asp | Thr | Gly | Glu | Trp | Pro | Ser | Thr | Glu | Pro | Asp | Asp | Leu | Asn | Ala | Ile | |
| | 450 | | | | | 455 | | | | | 460 | | | | | |
| GCC | GAA | GCC | TCA | AAC | ACC | GGA | ACT | GAA | GCA | CGT | TTC | ATG | GCC | CTA | GAT | 1440 |
| Ala | Glu | Ala | Ser | Asn | Thr | Gly | Thr | Glu | Ala | Arg | Phe | Met | Ala | Leu | Asp | |
| 465 | | | | | 470 | | | | | 475 | | | | | 480 | |
| GGC | TGG | GAA | ATA | CCC | GAG | TAC | AAT | CGT | ACT | TGG | AAG | CCT | GAA | TAA | | 1485 |
| Gly | Trp | Glu | Ile | Pro | Glu | Tyr | Asn | Arg | Thr | Trp | Lys | Pro | Glu | | | |
| | | | | 485 | | | | | 490 | | | | | | | |

( 2 ) INFORMATION FOR SEQ ID NO:4:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ile | Ile | Lys | Gly | Ser | Val | Pro | Gly | Lys | Ala | Gly | Gly | Lys | Pro | Arg |
| 1 | | | | 5 | | | | | 10 | | | | | 15 | |
| Ala | Thr | Ile | Phe | His | Ser | Ser | Ile | Ala | Thr | Leu | Leu | Leu | Thr | Thr | Val |
| | | | 20 | | | | | 25 | | | | | 30 | | |
| Ser | Leu | Ser | Gly | Val | Ala | Pro | Ala | Phe | Ala | Gln | Ala | Pro | Ser | Val | His |
| | | 35 | | | | | 40 | | | | | 45 | | | |

```
Gln His Val Ala Phe Thr Glu Glu Ile Gly Asp Leu Pro Asp Gly Ser
     50                  55                  60
Ser Tyr Met Ile Arg Val Pro Glu Asn Trp Asn Gly Val Leu Ile Arg
 65                  70                  75                  80
Asp Leu Asp Leu Val Ser Gly Thr Ser Asn Ser Asn Ala Ala Arg Tyr
                 85                  90                  95
Glu Thr Met Leu Lys Glu Gly Phe Ala Val Ala Gly Thr Ala Arg His
            100                 105                 110
Pro Leu Arg Gln Trp Gln Tyr Asp Pro Ala His Glu Ile Glu Asn Leu
            115                 120                 125
Asn His Val Leu Asp Thr Phe Glu Glu Asn Tyr Gly Ser Pro Glu Arg
    130                 135                 140
Val Ile Gln Tyr Gly Cys Ser Gly Gly Ala His Val Ser Leu Ala Val
145                 150                 155                 160
Ala Glu Asp Phe Ser Asp Arg Val Asp Gly Ser Val Ala Leu Ala Ala
                165                 170                 175
His Thr Pro Val Trp Ile Met Asn Ser Phe Leu Asp Gly Trp Phe Ser
            180                 185                 190
Leu Gln Ser Leu Ile Gly Glu Tyr Tyr Val Glu Ala Gly His Gly Pro
        195                 200                 205
Leu Ser Asp Leu Ala Ile Thr Lys Leu Pro Asn Asp Gly Ser Ser Asn
    210                 215                 220
Ser Ser Gly His Gly Met Glu Gly Asp Leu Pro Ala Ala Trp Arg Asn
225                 230                 235                 240
Ala Phe Thr Ala Ala Asn Ala Thr Pro Glu Gly Arg Ala Arg Met Ala
                245                 250                 255
Leu Ala Phe Ala Leu Gly Gln Trp Ser Pro Trp Leu Ala Asp Asn Thr
            260                 265                 270
Pro Gln Pro Asp Leu Asp Asp Pro Glu Ala Ile Ala Asp Ser Val Tyr
        275                 280                 285
Glu Ser Ala Met Arg Leu Ala Gly Ser Pro Gly Gly Glu Ala Arg Ile
    290                 295                 300
Met Phe Glu Asn Ala Ala Arg Gly Gln Gln Leu Ser Trp Asn Asp Asp
305                 310                 315                 320
Ile Asp Tyr Ala Asp Phe Trp Glu Asn Ser Asn Pro Ala Met Lys Ser
                325                 330                 335
Ala Val Gln Glu Leu Tyr Asp Thr Ala Gly Leu Asp Leu Gln Ser Asp
            340                 345                 350
Ile Glu Thr Val Asn Ser Gln Pro Arg Ile Glu Ala Ser Gln Tyr Ala
    355                 360                 365
Leu Asp Tyr Trp Asn Thr Pro Gly Arg Asn Val Ile Gly Asp Pro Glu
    370                 375                 380
Val Pro Val Leu Arg Leu His Met Ile Gly Asp Tyr Gln Ile Pro Tyr
385                 390                 395                 400
Ser Leu Val Gln Gly Tyr Ser Asp Leu Ile Ser Glu Asn Asn Asn Asp
                405                 410                 415
Asp Leu Tyr Arg Thr Ala Phe Val Gln Ser Thr Gly His Cys Asn Phe
            420                 425                 430
Thr Ala Ala Glu Ser Ser Ala Ala Ile Glu Val Met Met Gln Arg Leu
    435                 440                 445
Asp Thr Gly Glu Trp Pro Ser Thr Glu Pro Asp Asp Leu Asn Ala Ile
    450                 455                 460
Ala Glu Ala Ser Asn Thr Gly Thr Glu Ala Arg Phe Met Ala Leu Asp
```

| | | | | 465 | | | | | 470 | | | | | 475 | | | | 480 |
|---|---|---|---|---|---|---|---|---|---|---|---|---|---|---|---|---|---|---|
| Gly | Trp | Glu | Ile | Pro | Glu | Tyr | Asn | Arg | Thr | Trp | Lys | Pro | Glu | | | | | |
| | | | | 485 | | | | | 490 | | | | | | | | | |

(2) INFORMATION FOR SEQ ID NO:5:

(i) SEQUENCE CHARACTERISTICS:
        (A) LENGTH: 1620 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 136..1617

(xi) SEQUENCE DESCRIPTION: SEQ ID NO:5:

| GGATCCTTAG | GAATCTAAAC | ATTCTGGTTG | ACACTCCACA | TTTTGAATGT | CAGCATTTCG | 60 |
|---|---|---|---|---|---|---|
| GCCATGGCTG | CTATGCAGCC | TGTTATTGCA | TTTGAAATGG | AATAGATCAG | CAAACTTATC | 120 |

| GGGAGGATGA | GTATT | ATG | ATA | ATC | AAG | GGT | AGT | GTA | CCG | GGT | AAA | GCC | GGA | 171 |
|---|---|---|---|---|---|---|---|---|---|---|---|---|---|---|
| | | Met | Ile | Ile | Lys | Gly | Ser | Val | Pro | Gly | Lys | Ala | Gly | |
| | | 1 | | | 5 | | | | | 10 | | | | |

| GGA | AAA | CCT | CGA | GCG | ACC | ATC | TTT | CAT | AGT | TCT | ATT | GCA | ACG | CTA | CTT | 219 |
|---|---|---|---|---|---|---|---|---|---|---|---|---|---|---|---|---|
| Gly | Lys | Pro | Arg | Ala | Thr | Ile | Phe | His | Ser | Ser | Ile | Ala | Thr | Leu | Leu | |
| | 15 | | | | | 20 | | | | | 25 | | | | | |

| TTA | ACC | ACA | GTC | TCA | CTG | TCA | GGA | GTA | GCG | CCA | GCA | TTT | GCA | CAG | GCG | 267 |
|---|---|---|---|---|---|---|---|---|---|---|---|---|---|---|---|---|
| Leu | Thr | Thr | Val | Ser | Leu | Ser | Gly | Val | Ala | Pro | Ala | Phe | Ala | Gln | Ala | |
| | 30 | | | | 35 | | | | | 40 | | | | | | |

| CCG | TCT | GTG | CAC | CAA | CAC | GTC | GCC | TTC | ACT | GAG | GAA | ATT | GGA | GAC | CTT | 315 |
|---|---|---|---|---|---|---|---|---|---|---|---|---|---|---|---|---|
| Pro | Ser | Val | His | Gln | His | Val | Ala | Phe | Thr | Glu | Glu | Ile | Gly | Asp | Leu | |
| 45 | | | | 50 | | | | | 55 | | | | | | 60 | |

| CCC | GAC | GGC | TCA | AGT | TAC | ATG | ATC | CGT | GTG | CCG | GAG | AAC | TGG | AAC | GGC | 363 |
|---|---|---|---|---|---|---|---|---|---|---|---|---|---|---|---|---|
| Pro | Asp | Gly | Ser | Ser | Tyr | Met | Ile | Arg | Val | Pro | Glu | Asn | Trp | Asn | Gly | |
| | | | 65 | | | | | 70 | | | | | 75 | | | |

| GTG | TTA | ATT | CGC | GAC | CTA | GAC | CTT | GTC | AGC | GGC | ACC | AGC | AAT | TCT | AAC | 411 |
|---|---|---|---|---|---|---|---|---|---|---|---|---|---|---|---|---|
| Val | Leu | Ile | Arg | Asp | Leu | Asp | Leu | Val | Ser | Gly | Thr | Ser | Asn | Ser | Asn | |
| | | 80 | | | | | 85 | | | | | 90 | | | | |

| GCC | GCA | AGG | TAC | GAA | ACC | ATG | CTG | AAA | GAA | GGT | TTT | GCC | GTT | GCT | GGC | 459 |
|---|---|---|---|---|---|---|---|---|---|---|---|---|---|---|---|---|
| Ala | Ala | Arg | Tyr | Glu | Thr | Met | Leu | Lys | Glu | Gly | Phe | Ala | Val | Ala | Gly | |
| | | 95 | | | | | 100 | | | | | 105 | | | | |

| ACG | GCG | AGG | CAT | CCC | CTT | CGG | CAA | TGG | CAA | TAT | GAC | CCC | GCT | CAC | GAG | 507 |
|---|---|---|---|---|---|---|---|---|---|---|---|---|---|---|---|---|
| Thr | Ala | Arg | His | Pro | Leu | Arg | Gln | Trp | Gln | Tyr | Asp | Pro | Ala | His | Glu | |
| | 110 | | | | | 115 | | | | | 120 | | | | | |

| ATT | GAA | AAC | CTC | AAT | CAC | GTG | CTG | GAC | ACA | TTC | GAG | GAA | AAT | TAC | GGT | 555 |
|---|---|---|---|---|---|---|---|---|---|---|---|---|---|---|---|---|
| Ile | Glu | Asn | Leu | Asn | His | Val | Leu | Asp | Thr | Phe | Glu | Glu | Asn | Tyr | Gly | |
| 125 | | | | | 130 | | | | | 135 | | | | | 140 | |

| TCA | CCT | GAA | AGA | GTT | ATC | CAG | TAC | GGT | TGC | TCG | GGT | GGG | GCA | CAC | GTG | 603 |
|---|---|---|---|---|---|---|---|---|---|---|---|---|---|---|---|---|
| Ser | Pro | Glu | Arg | Val | Ile | Gln | Tyr | Gly | Cys | Ser | Gly | Gly | Ala | His | Val | |
| | | | | 145 | | | | | 150 | | | | | 155 | | |

| TCA | CTA | GCC | GTG | GCA | GAG | GAC | TTC | TCG | GAC | CGC | GTA | GAT | GGC | TCA | GTT | 651 |
|---|---|---|---|---|---|---|---|---|---|---|---|---|---|---|---|---|
| Ser | Leu | Ala | Val | Ala | Glu | Asp | Phe | Ser | Asp | Arg | Val | Asp | Gly | Ser | Val | |
| | | | 160 | | | | | 165 | | | | | 170 | | | |

| GCT | CTA | GCT | GCT | CAT | ACT | CCT | GTC | TGG | ATA | ATG | AAT | TCT | TTC | TTG | GAC | 699 |
|---|---|---|---|---|---|---|---|---|---|---|---|---|---|---|---|---|
| Ala | Leu | Ala | Ala | His | Thr | Pro | Val | Trp | Ile | Met | Asn | Ser | Phe | Leu | Asp | |
| | | 175 | | | | | 180 | | | | | 185 | | | | |

| GGA | TGG | TTT | TCG | CTG | CAG | TCT | CTG | ATC | GGC | GAG | TAC | TAT | GTA | GAA | GCT | 747 |
|---|---|---|---|---|---|---|---|---|---|---|---|---|---|---|---|---|
| Gly | Trp | Phe | Ser | Leu | Gln | Ser | Leu | Ile | Gly | Glu | Tyr | Tyr | Val | Glu | Ala | |
| | 190 | | | | | 195 | | | | | 200 | | | | | |

| GGT | CAC | GGC | CCA | CTT | TCG | GAT | CTC | GCT | ATT | ACG | AAA | CTG | CCC | AAT | GAT | 795 |
|---|---|---|---|---|---|---|---|---|---|---|---|---|---|---|---|---|
| Gly | His | Gly | Pro | Leu | Ser | Asp | Leu | Ala | Ile | Thr | Lys | Leu | Pro | Asn | Asp | |

```
     205                      210                      215                      220
GGT  AGC  TCT  AAT  TCG  AGC  GGT  CAT  GGA  ATG  GAA  GGA  GAT  CTT  CCT  GCC                843
Gly  Ser  Ser  Asn  Ser  Ser  Gly  His  Gly  Met  Glu  Gly  Asp  Leu  Pro  Ala
               225                      230                      235

GCG  TGG  CGC  AAC  GCG  TTC  ACC  GCT  GCT  AAC  GCC  ACA  CCT  GAG  GGT  CGC                891
Ala  Trp  Arg  Asn  Ala  Phe  Thr  Ala  Ala  Asn  Ala  Thr  Pro  Glu  Gly  Arg
               240                      245                      250

GCA  CGC  ATG  GCA  CTA  GCC  TTT  GCG  CTC  GGT  CAG  TGG  TCT  CCG  TGG  TTG                939
Ala  Arg  Met  Ala  Leu  Ala  Phe  Ala  Leu  Gly  Gln  Trp  Ser  Pro  Trp  Leu
          255                      260                      265

GCC  GAC  AAC  ACG  CCC  CAA  CCT  GAT  CTC  GAT  GAT  CCT  GAG  GCC  ATC  GCG                987
Ala  Asp  Asn  Thr  Pro  Gln  Pro  Asp  Leu  Asp  Asp  Pro  Glu  Ala  Ile  Ala
          270                      275                      280

GAT  TCC  GTA  TAT  GAG  TCT  GCC  ATG  CGA  CTT  GCA  GGA  AGC  CCT  GGG  GGA               1035
Asp  Ser  Val  Tyr  Glu  Ser  Ala  Met  Arg  Leu  Ala  Gly  Ser  Pro  Gly  Gly
285                      290                      295                      300

GAA  GCG  CGC  ATA  ATG  TTC  GAG  AAC  GCC  GCT  CGA  GGG  CAA  CAG  CTC  TCT               1083
Glu  Ala  Arg  Ile  Met  Phe  Glu  Asn  Ala  Ala  Arg  Gly  Gln  Gln  Leu  Ser
                    305                      310                      315

TGG  AAC  GAC  GAC  ATC  GAC  TAT  GCG  GAT  TTC  TGG  GAG  AAC  TCA  AAC  CCA               1131
Trp  Asn  Asp  Asp  Ile  Asp  Tyr  Ala  Asp  Phe  Trp  Glu  Asn  Ser  Asn  Pro
               320                      325                      330

GCC  ATG  AAG  AGC  GCC  GTT  CAG  GAG  CTG  TAC  GAC  ACG  GCC  GGC  CTT  GAT               1179
Ala  Met  Lys  Ser  Ala  Val  Gln  Glu  Leu  Tyr  Asp  Thr  Ala  Gly  Leu  Asp
               335                      340                      345

CTG  CAG  TCC  GAT  ATA  GAA  ACG  GTA  AAT  TCC  CAG  CCA  CGC  ATA  GAG  GCA               1227
Leu  Gln  Ser  Asp  Ile  Glu  Thr  Val  Asn  Ser  Gln  Pro  Arg  Ile  Glu  Ala
          350                      355                      360

TCG  CAG  TAT  GCG  CTC  GAC  TAC  TGG  AAC  ACG  CCA  GGT  CGC  AAT  GTC  ATT               1275
Ser  Gln  Tyr  Ala  Leu  Asp  Tyr  Trp  Asn  Thr  Pro  Gly  Arg  Asn  Val  Ile
365                      370                      375                      380

GGC  GAC  CCC  GAA  GTT  CCT  GTG  CTG  CGC  CTG  CAT  ATG  ATA  GGC  GAC  TAC               1323
Gly  Asp  Pro  Glu  Val  Pro  Val  Leu  Arg  Leu  His  Met  Ile  Gly  Asp  Tyr
               385                      390                      395

CAA  ATT  CCC  TAT  AGT  CTT  GTA  CAG  GGC  TAC  AGC  GAT  CTT  ATC  TCA  GAG               1371
Gln  Ile  Pro  Tyr  Ser  Leu  Val  Gln  Gly  Tyr  Ser  Asp  Leu  Ile  Ser  Glu
               400                      405                      410

AAC  AAC  AAT  GAT  GAC  TTG  TAC  AGA  ACT  GCT  TTT  GTG  CAA  TCC  ACT  GGA               1419
Asn  Asn  Asn  Asp  Asp  Leu  Tyr  Arg  Thr  Ala  Phe  Val  Gln  Ser  Thr  Gly
          415                      420                      425

CAC  TGC  AAT  TTC  ACA  GCT  GCA  GAA  AGT  TCC  GCT  GCG  ATT  GAG  GTC  ATG               1467
His  Cys  Asn  Phe  Thr  Ala  Ala  Glu  Ser  Ser  Ala  Ala  Ile  Glu  Val  Met
          430                      435                      440

ATG  CAA  CGG  CTT  GAC  ACG  GGT  GAG  TGG  CCG  AGC  ACC  GAG  CCG  GAT  GAT               1515
Met  Gln  Arg  Leu  Asp  Thr  Gly  Glu  Trp  Pro  Ser  Thr  Glu  Pro  Asp  Asp
445                      450                      455                      460

CTG  AAT  GCA  ATT  GCC  GAA  GCC  TCA  AAC  ACC  GGA  ACT  GAA  GCA  CGT  TTC               1563
Leu  Asn  Ala  Ile  Ala  Glu  Ala  Ser  Asn  Thr  Gly  Thr  Glu  Ala  Arg  Phe
               465                      470                      475

ATG  GCC  CTA  GAT  GGC  TGG  GAA  ATA  CCC  GAG  TAC  AAT  CGT  ACT  TGG  AAG               1611
Met  Ala  Leu  Asp  Gly  Trp  Glu  Ile  Pro  Glu  Tyr  Asn  Arg  Thr  Trp  Lys
               480                      485                      490

CCT  GAA  TAA                                                                                 1620
Pro  Glu
```

( 2 ) INFORMATION FOR SEQ ID NO:6:

( i ) SEQUENCE CHARACTERISTICS:
        ( A ) LENGTH: 3029 base pairs
        ( B ) TYPE: nucleic acid
        ( C ) STRANDEDNESS: single 5,543,497

43                                                                                                    44
-continued ( D ) TOPOLOGY: linear ( i i ) MOLECULE TYPE: DNA (genomic)

( i x ) FEATURE:
    ( A ) NAME/KEY: CDS
    ( B ) LOCATION: 136..1617

( x i ) SEQUENCE DESCRIPTION: SEQ ID NO:6:

```
GGATCCTTAG GAATCTAAAC ATTCTGGTTG ACACTCCACA TTTTGAATGT CAGCATTTCG        60

GCCATGGCTG CTATGCAGCC TGTTATTGCA TTTGAAATGG AATAGATCAG CAAACTTATC       120

GGGAGGATGA GTATT ATG ATA ATC AAG GGT AGT GTA CCG GGT AAA GCC GGA       171
                Met Ile Ile Lys Gly Ser Val Pro Gly Lys Ala Gly
                 1               5                       10

GGA AAA CCT CGA GCG ACC ATC TTT CAT AGT TCT ATT GCA ACG CTA CTT        219
Gly Lys Pro Arg Ala Thr Ile Phe His Ser Ser Ile Ala Thr Leu Leu
         15                  20                  25

TTA ACC ACA GTC TCA CTG TCA GGA GTA GCG CCA GCA TTT GCA CAG GCG        267
Leu Thr Thr Val Ser Leu Ser Gly Val Ala Pro Ala Phe Ala Gln Ala
     30                  35                  40

CCG TCT GTG CAC CAA CAC GTC GCC TTC ACT GAG GAA ATT GGA GAC CTT        315
Pro Ser Val His Gln His Val Ala Phe Thr Glu Glu Ile Gly Asp Leu
 45                  50                  55                      60

CCC GAC GGC TCA AGT TAC ATG ATC CGT GTG CCG GAG AAC TGG AAC GGC        363
Pro Asp Gly Ser Ser Tyr Met Ile Arg Val Pro Glu Asn Trp Asn Gly
                 65                  70                  75

GTG TTA ATT CGC GAC CTA GAC CTT GTC AGC GGC ACC AGC AAT TCT AAC        411
Val Leu Ile Arg Asp Leu Asp Leu Val Ser Gly Thr Ser Asn Ser Asn
             80                  85                  90

GCC GCA AGG TAC GAA ACC ATG CTG AAA GAA GGT TTT GCC GTT GCT GGC        459
Ala Ala Arg Tyr Glu Thr Met Leu Lys Glu Gly Phe Ala Val Ala Gly
         95                 100                 105

ACG GCG AGG CAT CCC CTT CGG CAA TGG CAA TAT GAC CCC GCT CAC GAG        507
Thr Ala Arg His Pro Leu Arg Gln Trp Gln Tyr Asp Pro Ala His Glu
     110                 115                 120

ATT GAA AAC CTC AAT CAC GTG CTG GAC ACA TTC GAG GAA AAT TAC GGT        555
Ile Glu Asn Leu Asn His Val Leu Asp Thr Phe Glu Glu Asn Tyr Gly
125                 130                 135                 140

TCA CCT GAA AGA GTT ATC CAG TAC GGT TGC TCG GGT GGG GCA CAC GTG        603
Ser Pro Glu Arg Val Ile Gln Tyr Gly Cys Ser Gly Gly Ala His Val
             145                 150                 155

TCA CTA GCC GTG GCA GAG GAC TTC TCG GAC CGC GTA GAT GGC TCA GTT        651
Ser Leu Ala Val Ala Glu Asp Phe Ser Asp Arg Val Asp Gly Ser Val
         160                 165                 170

GCT CTA GCT GCT CAT ACT CCT GTC TGG ATA ATG AAT TCT TTC TTG GAC        699
Ala Leu Ala Ala His Thr Pro Val Trp Ile Met Asn Ser Phe Leu Asp
     175                 180                 185

GGA TGG TTT TCG CTG CAG TCT CTG ATC GGC GAG TAC TAT GTA GAA GCT        747
Gly Trp Phe Ser Leu Gln Ser Leu Ile Gly Glu Tyr Tyr Val Glu Ala
 190                 195                 200

GGT CAC GGC CCA CTT TCG GAT CTC GCT ATT ACG AAA CTG CCC AAT GAT        795
Gly His Gly Pro Leu Ser Asp Leu Ala Ile Thr Lys Leu Pro Asn Asp
205                 210                 215                 220

GGT AGC TCT AAT TCG AGC GGT CAT GGA ATG GAA GGA GAT CTT CCT GCC        843
Gly Ser Ser Asn Ser Ser Gly His Gly Met Glu Gly Asp Leu Pro Ala
             225                 230                 235

GCG TGG CGC AAC GCG TTC ACC GCT GCT AAC GCC ACA CCT GAG GGT CGC        891
Ala Trp Arg Asn Ala Phe Thr Ala Ala Asn Ala Thr Pro Glu Gly Arg
         240                 245                 250

GCA CGC ATG GCA CTA GCC TTT GCG CTC GGT CAG TGG TCT CCG TGG TTG        939
Ala Arg Met Ala Leu Ala Phe Ala Leu Gly Gln Trp Ser Pro Trp Leu
     255                 260                 265
```

|  |  |  |  |  |  |  |  |  |  |  |  |  |  |  |  |
|---|---|---|---|---|---|---|---|---|---|---|---|---|---|---|---|
|  |  |  |  | 255 |  |  |  |  | 260 |  |  |  |  | 265 |  |
| GCC | GAC | AAC | ACG | CCC | CAA | CCT | GAT | CTC | GAT | GAT | CCT | GAG | GCC | ATC | GCG | 987
| Ala | Asp | Asn | Thr | Pro | Gln | Pro | Asp | Leu | Asp | Asp | Pro | Glu | Ala | Ile | Ala |
|  | 270 |  |  |  | 275 |  |  |  |  | 280 |  |  |  |  |  |
| GAT | TCC | GTA | TAT | GAG | TCT | GCC | ATG | CGA | CTT | GCA | GGA | AGC | CCT | GGG | GGA | 1035
| Asp | Ser | Val | Tyr | Glu | Ser | Ala | Met | Arg | Leu | Ala | Gly | Ser | Pro | Gly | Gly |
| 285 |  |  |  |  | 290 |  |  |  |  | 295 |  |  |  |  | 300 |
| GAA | GCG | CGC | ATA | ATG | TTC | GAG | AAC | GCC | GCT | CGA | GGG | CAA | CAG | CTC | TCT | 1083
| Glu | Ala | Arg | Ile | Met | Phe | Glu | Asn | Ala | Ala | Arg | Gly | Gln | Gln | Leu | Ser |
|  |  |  |  | 305 |  |  |  |  | 310 |  |  |  |  | 315 |  |
| TGG | AAC | GAC | GAC | ATC | GAC | TAT | GCG | GAT | TTC | TGG | GAG | AAC | TCA | AAC | CCA | 1131
| Trp | Asn | Asp | Asp | Ile | Asp | Tyr | Ala | Asp | Phe | Trp | Glu | Asn | Ser | Asn | Pro |
|  |  |  | 320 |  |  |  |  | 325 |  |  |  |  | 330 |  |  |
| GCC | ATG | AAG | AGC | GCC | GTT | CAG | GAG | CTG | TAC | GAC | ACG | GCC | GGC | CTT | GAT | 1179
| Ala | Met | Lys | Ser | Ala | Val | Gln | Glu | Leu | Tyr | Asp | Thr | Ala | Gly | Leu | Asp |
|  |  | 335 |  |  |  |  | 340 |  |  |  |  | 345 |  |  |  |
| CTG | CAG | TCC | GAT | ATA | GAA | ACG | GTA | AAT | TCC | CAG | CCA | CGC | ATA | GAG | GCA | 1227
| Leu | Gln | Ser | Asp | Ile | Glu | Thr | Val | Asn | Ser | Gln | Pro | Arg | Ile | Glu | Ala |
|  | 350 |  |  |  |  | 355 |  |  |  |  | 360 |  |  |  |  |
| TCG | CAG | TAT | GCG | CTC | GAC | TAC | TGG | AAC | ACG | CCA | GGT | CGC | AAT | GTC | ATT | 1275
| Ser | Gln | Tyr | Ala | Leu | Asp | Tyr | Trp | Asn | Thr | Pro | Gly | Arg | Asn | Val | Ile |
| 365 |  |  |  |  | 370 |  |  |  |  | 375 |  |  |  |  | 380 |
| GGC | GAC | CCC | GAA | GTT | CCT | GTG | CTG | CGC | CTG | CAT | ATG | ATA | GGC | GAC | TAC | 1323
| Gly | Asp | Pro | Glu | Val | Pro | Val | Leu | Arg | Leu | His | Met | Ile | Gly | Asp | Tyr |
|  |  |  |  | 385 |  |  |  |  | 390 |  |  |  |  | 395 |  |
| CAA | ATT | CCC | TAT | AGT | CTT | GTA | CAG | GGC | TAC | AGC | GAT | CTT | ATC | TCA | GAG | 1371
| Gln | Ile | Pro | Tyr | Ser | Leu | Val | Gln | Gly | Tyr | Ser | Asp | Leu | Ile | Ser | Glu |
|  |  |  | 400 |  |  |  |  | 405 |  |  |  |  | 410 |  |  |
| AAC | AAC | AAT | GAT | GAC | TTG | TAC | AGA | ACT | GCT | TTT | GTG | CAA | TCC | ACT | GGA | 1419
| Asn | Asn | Asn | Asp | Asp | Leu | Tyr | Arg | Thr | Ala | Phe | Val | Gln | Ser | Thr | Gly |
|  |  | 415 |  |  |  |  | 420 |  |  |  |  | 425 |  |  |  |
| CAC | TGC | AAT | TTC | ACA | GCT | GCA | GAA | AGT | TCC | GCT | GCG | ATT | GAG | GTC | ATG | 1467
| His | Cys | Asn | Phe | Thr | Ala | Ala | Glu | Ser | Ser | Ala | Ala | Ile | Glu | Val | Met |
|  | 430 |  |  |  |  | 435 |  |  |  |  | 440 |  |  |  |  |
| ATG | CAA | CGG | CTT | GAC | ACG | GGT | GAG | TGG | CCG | AGC | ACC | GAG | CCG | GAT | GAT | 1515
| Met | Gln | Arg | Leu | Asp | Thr | Gly | Glu | Trp | Pro | Ser | Thr | Glu | Pro | Asp | Asp |
| 445 |  |  |  |  | 450 |  |  |  |  | 455 |  |  |  |  | 460 |
| CTG | AAT | GCA | ATT | GCC | GAA | GCC | TCA | AAC | ACC | GGA | ACT | GAA | GCA | CGT | TTC | 1563
| Leu | Asn | Ala | Ile | Ala | Glu | Ala | Ser | Asn | Thr | Gly | Thr | Glu | Ala | Arg | Phe |
|  |  |  |  | 465 |  |  |  |  | 470 |  |  |  |  | 475 |  |
| ATG | GCC | CTA | GAT | GGC | TGG | GAA | ATA | CCC | GAG | TAC | AAT | CGT | ACT | TGG | AAG | 1611
| Met | Ala | Leu | Asp | Gly | Trp | Glu | Ile | Pro | Glu | Tyr | Asn | Arg | Thr | Trp | Lys |
|  |  |  | 480 |  |  |  |  | 485 |  |  |  |  | 490 |  |  |
| CCT | GAA | TAATCACCAT | TCTGGAGGCT | CACGTTCGCG | AAGGGTTGCG | GCGAAGAAAA |  |  |  |  |  |  |  |  |  | 1667
| Pro | Glu |  |  |  |  |  |  |  |  |  |  |  |  |  |  |

```
CATGCGCCGC AACCTATCCT CCAAACAAGG GCCAGTTCAA CGACGAACAA GCCAGACCGG    1727
CGCAAGCCGC GCTAATCTAA TTCACCGCTC CAACCCGCGA TCTCGCGACC GCCCGCGCTG    1787
CATGTCGAGC TTCTGTTGCT GCGCCCGCTC AAGCGTATAA TCACGCCGGA TAATCGTTTC    1847
CCGCGCTTTG TTCGTGATCC TTGCAACGTC CTTGATGCGA TCGACGTTAC GGGCTGTCTC    1907
TGAAGGCTGT GAGCGTGTGC GATCAAGCGC CTGATCGATA TCGCGATGAT TGCTTGATCC    1967
GAACCGGATC TGCATAGCCC GGGCAATACG TTTGGCTTCA TCAAGCGCCT GTTTGCCATC    2027
AGCCGTCTTT TCGAGCTGAT CGACAAAGCC CGTCCGTGCC TTCGCATCCT TGATCTGATC    2087
GAGCTGCCTG AGCAGGGTTT CGCTGCGAGG TGAGAGGCCA GGAATCTCGA CGCGATCATT    2147
ATTGTCACGC CGCCATTGTT CGGCTTCCTT TTCCTCGGCA AAGCGCCGCG TCCAGGTCTT    2207
CCCCGCCGCG TCCAGATGCG AACTCATCGC CTCGGCCCGC TTGAGGGCAT TTTTTGCGCT    2267
```

| CGGCATTGGC | ACCGAACAGG | CCGAACTTGC | CGCGCAGCTG | TTGATTTCTG | CTGAGAAGTG | 2327 |
| ACCCGGTATT | GGAGTGAACC | CCTGGGACTG | GACCAGCGGG | GAAGAAAAGC | TGATACGCTC | 2387 |
| TGTGGGCCTT | GAATGGAGAA | GGTCCATGTC | ACCAAGAGGT | CCCTACCGCC | GTCACTCGAT | 2447 |
| GCAGTTCAAG | CGTAAGCGCC | AAGCCTGGCC | CGTCTGGTGA | TGGCTGCCTT | TGAGCGCTAT | 2507 |
| CGACACCCCG | GAGTTAGTGA | TGGGTGTCAT | GTTCTATGTC | TGCGACTATG | CCTGCAGATA | 2567 |
| GAAGTTTCCA | GTTGATCGAG | GCGGTTCCGG | ATCGGATGGA | GGGCGCTCCG | GTTGCGCGGC | 2627 |
| GACGCCGGTG | GTCGGACGCG | TTCAAGGCCG | AGATGGTAGC | GCGCAGCTTC | GAACCTGGAA | 2687 |
| CGAATGTGTC | GGCACTGGCG | CGCGAGATCG | GCATCCAGTC | CTCGCAGTTG | TTCGGCTGGC | 2747 |
| GCGCCGAGGC | CCTCAAGCGC | GGAGAGGTGG | AAAGGCGCGA | TGTTGATATC | GTTGCAACGC | 2807 |
| AAGCCTCTCG | CTTGGTGAGC | GGGACGGTCG | AGATCGCGGT | CAACGACACG | GTGATCCGGG | 2867 |
| TCGGCATTGA | TATCGGGGAA | GACCATTTGC | GGCGCGTGAT | CCGCGCTGTG | CGGTCGGCAT | 2927 |
| GATCCCTGCG | GGTGTGAAGG | TCTATCTGGC | CAGCCAGCCG | GTAGACTTCA | GGAAAGGTCC | 2987 |
| AGACGGCCTT | GTTGGCCTGG | TGCGCGATGC | TGGAGCGGAT | CC | | 3029 |

( 2 ) INFORMATION FOR SEQ ID NO:7:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| GGATCCTTAG | GAATCTAAAC | ATTCTGGTTG | ACACTCCACA | TTTGAATGT | CAGCATTTCG | 60 |
| GCCATGGCTG | CTATGCAGCC | TGTTATTGCA | TTTGAAATGG | AATAGATCAG | CAAACTTATC | 120 |
| GGGAGGATGA | GTATT | | | | | 135 |

( 2 ) INFORMATION FOR SEQ ID NO:8:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..126

( x i ) SEQUENCE DESCRIPTION: SEQ ID NO:8:

```
ATG  ATA  ATC  AAG  GGT  AGT  GTA  CCG  GGT  AAA  GCC  GGA  GGA  AAA  CCT  CGA    48
Met  Ile  Ile  Lys  Gly  Ser  Val  Pro  Gly  Lys  Ala  Gly  Gly  Lys  Pro  Arg
 1                  5                   10                      15

GCG  ACC  ATC  TTT  CAT  AGT  TCT  ATT  GCA  ACG  CTA  CTT  TTA  ACC  ACA  GTC    96
Ala  Thr  Ile  Phe  His  Ser  Ser  Ile  Ala  Thr  Leu  Leu  Leu  Thr  Thr  Val
                    20                      25                      30

TCA  CTG  TCA  GGA  GTA  GCG  CCA  GCA  TTT  GCA                                  126
Ser  Leu  Ser  Gly  Val  Ala  Pro  Ala  Phe  Ala
             35                      40
```

( 2 ) INFORMATION FOR SEQ ID NO:9:

( i ) SEQUENCE CHARACTERISTICS:
        ( A ) LENGTH: 42 amino acids ( B ) TYPE: amino acid
( D ) TOPOLOGY: linear ( i i ) MOLECULE TYPE: protein ( x i ) SEQUENCE DESCRIPTION: SEQ ID NO:9:

| Met | Ile | Ile | Lys | Gly | Ser | Val | Pro | Gly | Lys | Ala | Gly | Gly | Lys | Pro | Arg |
|---|---|---|---|---|---|---|---|---|---|---|---|---|---|---|---|
| 1 | | | | 5 | | | | | 10 | | | | | 15 | |
| Ala | Thr | Ile | Phe | His | Ser | Ser | Ile | Ala | Thr | Leu | Leu | Leu | Thr | Thr | Val |
| | | | 20 | | | | | 25 | | | | | 30 | | |
| Ser | Leu | Ser | Gly | Val | Ala | Pro | Ala | Phe | Ala |
| | | | 35 | | | | 40 | | |

( 2 ) INFORMATION FOR SEQ ID NO:10:

( i ) SEQUENCE CHARACTERISTICS:
( A ) LENGTH: 1409 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

| TCACCATTCT | GGAGGCTCAC | GTTCGCGAAG | GGTTGCGGCG | AAGAAAACAT | GCGCCGCAAC | 60 |
| CTATCCTCCA | AACAAGGGCC | AGTTCAACGA | CGAACAAGCC | AGACCGGCGC | AAGCCGCGCT | 120 |
| AATCTAATTC | ACCGCTCCAA | CCCGCGATCT | CGCGACCGCC | CGCGCTGCAT | GTCGAGCTTC | 180 |
| TGTTGCTGCG | CCCGCTCAAG | CGTATAATCA | CGCCGGATAA | TCGTTTCCCG | CGCTTTGTTC | 240 |
| GTGATCCTTG | CAACGTCCTT | GATGCGATCG | ACGTTACGGG | CTGTCTCTGA | AGGCTGTGAG | 300 |
| CGTGTGCGAT | CAAGCGCCTG | ATCGATATCG | CGATGATTGC | TTGATCCGAA | CCGGATCTGC | 360 |
| ATAGCCCGGG | CAATACGTTT | GGCTTCATCA | AGCGCCTGTT | TGCCATCAGC | CGTCTTTTCG | 420 |
| AGCTGATCGA | CAAAGCCCGT | CCGTGCCTTC | GCATCCTTGA | TCTGATCGAG | CTGCCTGAGC | 480 |
| AGGGTTTCGC | TGCGAGGTGA | GAGGCCAGGA | ATCTCGACGC | GATCATTATT | GTCACGCCGC | 540 |
| CATTGTTCGG | CTTCCTTTTC | CTCGGCAAAG | CGCCGCGTCC | AGGTCTTCCC | CGCCGCGTCC | 600 |
| AGATGCGAAC | TCATCGCCTC | GGCCCGCTTG | AGGGCATTTT | TTGCGCTCGG | CATTGGCACC | 660 |
| GAACAGGCCG | AACTTGCCGC | GCAGCTGTTG | ATTTCTGCTG | AGAAGTGACC | CGGTATTGGA | 720 |
| GTGAACCCCT | GGGACTGGAC | CAGCGGGGAA | GAAAAGCTGA | TACGCTCTGT | GGGCCTTGAA | 780 |
| TGGAGAAGGT | CCATGTCACC | AAGAGGTCCC | TACCGCCGTC | ACTCGATGCA | GTTCAAGCGT | 840 |
| AAGCGCCAAG | CCTGGCCCGT | CTGGTGATGG | CTGCCTTTGA | GCGCTATCGA | CACCCCGGAG | 900 |
| TTAGTGATGG | GTGTCATGTT | CTATGTCTGC | GACTATGCCT | GCAGATAGAA | GTTTCCAGTT | 960 |
| GATCGAGGCG | GTTCCGGATC | GGATGGAGGG | CGCTCCGGTT | GCGCGGCGAC | GCCGGTGGTC | 1020 |
| GGACGCGTTC | AAGGCCGAGA | TGGTAGCGCG | CAGCTTCGAA | CCTGGAACGA | ATGTGTCGGC | 1080 |
| ACTGGCGCGC | GAGATCGGCA | TCCAGTCCTC | GCAGTTGTTC | GGCTGGCGCG | CCGAGGCCCT | 1140 |
| CAAGCGCGGA | GAGGTGGAAA | GGCGCGATGT | TGATATCGTT | GCAACGCAAG | CCTCTCGCTT | 1200 |
| GGTGAGCGGG | ACGGTCGAGA | TCGCGGTCAA | CGACACGGTG | ATCCGGGTCG | GCATTGATAT | 1260 |
| CGGGGAAGAC | CATTTGCGGC | GCGTGATCCG | CGCTGTGCGG | TCGGCATGAT | CCCTGCGGGT | 1320 |
| GTGAAGGTCT | ATCTGGCCAG | CCAGCCGGTA | GACTTCAGGA | AAGGTCCAGA | CGGCCTTGTT | 1380 |
| GGCCTGGTGC | GCGATGCTGG | AGCGGATCC | | | | 1409 |

( 2 ) INFORMATION FOR SEQ ID NO:11:

( i ) SEQUENCE CHARACTERISTICS:
  ( A ) LENGTH: 1362 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 1..1359

( x i ) SEQUENCE DESCRIPTION: SEQ ID NO:11:

```
ATG CAG GCG CCG TCT GTG CAC CAA CAC GTC GCC TTC ACT GAG GAA ATT        48
Met Gln Ala Pro Ser Val His Gln His Val Ala Phe Thr Glu Glu Ile
 1               5                  10                  15

GGA GAC CTT CCC GAC GGC TCA AGT TAC ATG ATC CGT GTG CCG GAG AAC        96
Gly Asp Leu Pro Asp Gly Ser Ser Tyr Met Ile Arg Val Pro Glu Asn
             20                  25                  30

TGG AAC GGC GTG TTA ATT CGC GAC CTA GAC CTT GTC AGC GGC ACC AGC       144
Trp Asn Gly Val Leu Ile Arg Asp Leu Asp Leu Val Ser Gly Thr Ser
         35                  40                  45

AAT TCT AAC GCC GCA AGG TAC GAA ACC ATG CTG AAA GAA GGT TTT GCC       192
Asn Ser Asn Ala Ala Arg Tyr Glu Thr Met Leu Lys Glu Gly Phe Ala
     50                  55                  60

GTT GCT GGC ACG GCG AGG CAT CCC CTT CGG CAA TGG CAA TAT GAC CCC       240
Val Ala Gly Thr Ala Arg His Pro Leu Arg Gln Trp Gln Tyr Asp Pro
 65                  70                  75                  80

GCT CAC GAG ATT GAA AAC CTC AAT CAC GTG CTG GAC ACA TTC GAG GAA       288
Ala His Glu Ile Glu Asn Leu Asn His Val Leu Asp Thr Phe Glu Glu
                 85                  90                  95

AAT TAC GGT TCA CCT GAA AGA GTT ATC CAG TAC GGT TGC TCG GGT GGG       336
Asn Tyr Gly Ser Pro Glu Arg Val Ile Gln Tyr Gly Cys Ser Gly Gly
            100                 105                 110

GCA CAC GTG TCA CTA GCC GTG GCA GAG GAC TTC TCG GAC CGC GTA GAT       384
Ala His Val Ser Leu Ala Val Ala Glu Asp Phe Ser Asp Arg Val Asp
        115                 120                 125

GGC TCA GTT GCT CTA GCT GCT CAT ACT CCT GTC TGG ATA ATG AAT TCT       432
Gly Ser Val Ala Leu Ala Ala His Thr Pro Val Trp Ile Met Asn Ser
    130                 135                 140

TTC TTG GAC GGA TGG TTT TCG CTG CAG TCT CTG ATC GGC GAG TAC TAT       480
Phe Leu Asp Gly Trp Phe Ser Leu Gln Ser Leu Ile Gly Glu Tyr Tyr
145                 150                 155                 160

GTA GAA GCT GGT CAC GGC CCA CTT TCG GAT CTC GCT ATT ACG AAA CTG       528
Val Glu Ala Gly His Gly Pro Leu Ser Asp Leu Ala Ile Thr Lys Leu
                165                 170                 175

CCC AAT GAT GGT AGC TCT AAT TCG AGC GGT CAT GGA ATG GAA GGA GAT       576
Pro Asn Asp Gly Ser Ser Asn Ser Ser Gly His Gly Met Glu Gly Asp
            180                 185                 190

CTT CCT GCC GCG TGG CGC AAC GCG TTC ACC GCT GCT AAC GCC ACA CCT       624
Leu Pro Ala Ala Trp Arg Asn Ala Phe Thr Ala Ala Asn Ala Thr Pro
        195                 200                 205

GAG GGT CGC GCA CGC ATG GCA CTA GCC TTT GCG CTC GGT CAG TGG TCT       672
Glu Gly Arg Ala Arg Met Ala Leu Ala Phe Ala Leu Gly Gln Trp Ser
    210                 215                 220

CCG TGG TTG GCC GAC AAC ACG CCC CAA CCT GAT CTC GAT GAT CCT GAG       720
Pro Trp Leu Ala Asp Asn Thr Pro Gln Pro Asp Leu Asp Asp Pro Glu
225                 230                 235                 240

GCC ATC GCG GAT TCC GTA TAT GAG TCT GCC ATG CGA CTT GCA GGA AGC       768
Ala Ile Ala Asp Ser Val Tyr Glu Ser Ala Met Arg Leu Ala Gly Ser
                245                 250                 255

CCT GGG GGA GAA GCG CGC ATA ATG TTC GAG AAC GCC GCT CGA GGG CAA       816
Pro Gly Gly Glu Ala Arg Ile Met Phe Glu Asn Ala Ala Arg Gly Gln
```

|  |  |  |  |  |  |  |  |  |  |  |  |  |  |  |  |
|---|---|---|---|---|---|---|---|---|---|---|---|---|---|---|---|
|  |  |  | 260 |  |  |  | 265 |  |  |  | 270 |  |  |  |  |
| CAG | CTC | TCT | TGG | AAC | GAC | GAC | ATC | GAC | TAT | GCG | GAT | TTC | TGG | GAG | AAC | 864 |
| Gln | Leu | Ser | Trp | Asn | Asp | Asp | Ile | Asp | Tyr | Ala | Asp | Phe | Trp | Glu | Asn |
|  |  | 275 |  |  |  |  | 280 |  |  |  |  | 285 |  |  |  |
| TCA | AAC | CCA | GCC | ATG | AAG | AGC | GCC | GTT | CAG | GAG | CTG | TAC | GAC | ACG | GCC | 912 |
| Ser | Asn | Pro | Ala | Met | Lys | Ser | Ala | Val | Gln | Glu | Leu | Tyr | Asp | Thr | Ala |
|  | 290 |  |  |  |  | 295 |  |  |  |  | 300 |  |  |  |  |
| GGC | CTT | GAT | CTG | CAG | TCC | GAT | ATA | GAA | ACG | GTA | AAT | TCC | CAG | CCA | CGC | 960 |
| Gly | Leu | Asp | Leu | Gln | Ser | Asp | Ile | Glu | Thr | Val | Asn | Ser | Gln | Pro | Arg |
| 305 |  |  |  |  | 310 |  |  |  |  | 315 |  |  |  |  | 320 |
| ATA | GAG | GCA | TCG | CAG | TAT | GCG | CTC | GAC | TAC | TGG | AAC | ACG | CCA | GGT | CGC | 1008 |
| Ile | Glu | Ala | Ser | Gln | Tyr | Ala | Leu | Asp | Tyr | Trp | Asn | Thr | Pro | Gly | Arg |
|  |  |  |  | 325 |  |  |  |  | 330 |  |  |  |  | 335 |  |
| AAT | GTC | ATT | GGC | GAC | CCC | GAA | GTT | CCT | GTG | CTG | CGC | CTG | CAT | ATG | ATA | 1056 |
| Asn | Val | Ile | Gly | Asp | Pro | Glu | Val | Pro | Val | Leu | Arg | Leu | His | Met | Ile |
|  |  |  | 340 |  |  |  |  | 345 |  |  |  |  | 350 |  |  |
| GGC | GAC | TAC | CAA | ATT | CCC | TAT | AGT | CTT | GTA | CAG | GGC | TAC | AGC | GAT | CTT | 1104 |
| Gly | Asp | Tyr | Gln | Ile | Pro | Tyr | Ser | Leu | Val | Gln | Gly | Tyr | Ser | Asp | Leu |
|  |  | 355 |  |  |  |  | 360 |  |  |  |  | 365 |  |  |  |
| ATC | TCA | GAG | AAC | AAC | AAT | GAT | GAC | TTG | TAC | AGA | ACT | GCT | TTT | GTG | CAA | 1152 |
| Ile | Ser | Glu | Asn | Asn | Asn | Asp | Asp | Leu | Tyr | Arg | Thr | Ala | Phe | Val | Gln |
|  | 370 |  |  |  |  | 375 |  |  |  |  | 380 |  |  |  |  |
| TCC | ACT | GGA | CAC | TGC | AAT | TTC | ACA | GCT | GCA | GAA | AGT | TCC | GCT | GCG | ATT | 1200 |
| Ser | Thr | Gly | His | Cys | Asn | Phe | Thr | Ala | Ala | Glu | Ser | Ser | Ala | Ala | Ile |
| 385 |  |  |  | 390 |  |  |  |  | 395 |  |  |  |  |  | 400 |
| GAG | GTC | ATG | ATG | CAA | CGG | CTT | GAC | ACG | GGT | GAG | TGG | CCG | AGC | ACC | GAG | 1248 |
| Glu | Val | Met | Met | Gln | Arg | Leu | Asp | Thr | Gly | Glu | Trp | Pro | Ser | Thr | Glu |
|  |  |  |  | 405 |  |  |  |  | 410 |  |  |  |  | 415 |  |
| CCG | GAT | GAT | CTG | AAT | GCA | ATT | GCC | GAA | GCC | TCA | AAC | ACC | GGA | ACT | GAA | 1296 |
| Pro | Asp | Asp | Leu | Asn | Ala | Ile | Ala | Glu | Ala | Ser | Asn | Thr | Gly | Thr | Glu |
|  |  |  | 420 |  |  |  |  | 425 |  |  |  |  | 430 |  |  |
| GCA | CGT | TTC | ATG | GCC | CTA | GAT | GGC | TGG | GAA | ATA | CCC | GAG | TAC | AAT | CGT | 1344 |
| Ala | Arg | Phe | Met | Ala | Leu | Asp | Gly | Trp | Glu | Ile | Pro | Glu | Tyr | Asn | Arg |
|  |  | 435 |  |  |  |  | 440 |  |  |  |  | 445 |  |  |  |
| ACT | TGG | AAG | CCT | GAA | TAA |  |  |  |  |  |  |  |  |  |  | 1362 |
| Thr | Trp | Lys | Pro | Glu |  |  |  |  |  |  |  |  |  |  |  |
| 450 |  |  |  |  |  |  |  |  |  |  |  |  |  |  |  |

( 2 ) INFORMATION FOR SEQ ID NO:12:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Gln | Ala | Pro | Ser | Val | His | Gln | His | Val | Ala | Phe | Thr | Glu | Glu | Ile |
|---|---|---|---|---|---|---|---|---|---|---|---|---|---|---|---|
| 1 |  |  |  | 5 |  |  |  |  | 10 |  |  |  |  | 15 |  |
| Gly | Asp | Leu | Pro | Asp | Gly | Ser | Ser | Tyr | Met | Ile | Arg | Val | Pro | Glu | Asn |
|  |  |  | 20 |  |  |  |  | 25 |  |  |  |  | 30 |  |  |
| Trp | Asn | Gly | Val | Leu | Ile | Arg | Asp | Leu | Asp | Leu | Val | Ser | Gly | Thr | Ser |
|  |  | 35 |  |  |  |  | 40 |  |  |  |  | 45 |  |  |  |
| Asn | Ser | Asn | Ala | Ala | Arg | Tyr | Glu | Thr | Met | Leu | Lys | Glu | Gly | Phe | Ala |
|  | 50 |  |  |  |  | 55 |  |  |  |  | 60 |  |  |  |  |
| Val | Ala | Gly | Thr | Ala | Arg | His | Pro | Leu | Arg | Gln | Trp | Gln | Tyr | Asp | Pro |
| 65 |  |  |  |  | 70 |  |  |  |  | 75 |  |  |  |  | 80 |
| Ala | His | Glu | Ile | Glu | Asn | Leu | Asn | His | Val | Leu | Asp | Thr | Phe | Glu | Glu |
|  |  |  |  | 85 |  |  |  |  | 90 |  |  |  |  | 95 |  |

```
Asn Tyr Gly Ser Pro Glu Arg Val Ile Gln Tyr Gly Cys Ser Gly Gly
            100                 105                 110
Ala His Val Ser Leu Ala Val Ala Glu Asp Phe Ser Asp Arg Val Asp
        115                 120             125
Gly Ser Val Ala Leu Ala Ala His Thr Pro Val Trp Ile Met Asn Ser
    130                 135                 140
Phe Leu Asp Gly Trp Phe Ser Leu Gln Ser Leu Ile Gly Glu Tyr Tyr
145                     150             155                     160
Val Glu Ala Gly His Gly Pro Leu Ser Asp Leu Ala Ile Thr Lys Leu
                165                 170                 175
Pro Asn Asp Gly Ser Ser Asn Ser Ser Gly His Gly Met Glu Gly Asp
            180                 185             190
Leu Pro Ala Ala Trp Arg Asn Ala Phe Thr Ala Ala Asn Ala Thr Pro
        195                 200                 205
Glu Gly Arg Ala Arg Met Ala Leu Ala Phe Ala Leu Gly Gln Trp Ser
        210                 215                 220
Pro Trp Leu Ala Asp Asn Thr Pro Gln Pro Asp Leu Asp Asp Pro Glu
225                 230                 235                 240
Ala Ile Ala Asp Ser Val Tyr Glu Ser Ala Met Arg Leu Ala Gly Ser
                245                 250                 255
Pro Gly Gly Glu Ala Arg Ile Met Phe Glu Asn Ala Ala Arg Gly Gln
            260                 265                 270
Gln Leu Ser Trp Asn Asp Asp Ile Asp Tyr Ala Asp Phe Trp Glu Asn
        275                 280                 285
Ser Asn Pro Ala Met Lys Ser Ala Val Gln Glu Leu Tyr Asp Thr Ala
    290                 295                 300
Gly Leu Asp Leu Gln Ser Asp Ile Glu Thr Val Asn Ser Gln Pro Arg
305                 310                 315                 320
Ile Glu Ala Ser Gln Tyr Ala Leu Asp Tyr Trp Asn Thr Pro Gly Arg
                325                 330                 335
Asn Val Ile Gly Asp Pro Glu Val Pro Val Leu Arg Leu His Met Ile
            340                 345                 350
Gly Asp Tyr Gln Ile Pro Tyr Ser Leu Val Gln Gly Tyr Ser Asp Leu
        355                 360                 365
Ile Ser Glu Asn Asn Asn Asp Asp Leu Tyr Arg Thr Ala Phe Val Gln
    370                 375                 380
Ser Thr Gly His Cys Asn Phe Thr Ala Ala Glu Ser Ser Ala Ala Ile
385                 390                 395                 400
Glu Val Met Met Gln Arg Leu Asp Thr Gly Glu Trp Pro Ser Thr Glu
                405                 410                 415
Pro Asp Asp Leu Asn Ala Ile Ala Glu Ala Ser Asn Thr Gly Thr Glu
            420                 425                 430
Ala Arg Phe Met Ala Leu Asp Gly Trp Glu Ile Pro Glu Tyr Asn Arg
        435                 440                 445
Thr Trp Lys Pro Glu
        450
```